(12) United States Patent
Grote et al.

(10) Patent No.: US 7,709,637 B2
(45) Date of Patent: *May 4, 2010

(54) 5-PHENYLPYRIMIDINES, THEIR PREPARATION, INTERMEDIATES FOR THEIR PREPARATION, AND THEIR USE FOR CONTROLLING HARMFUL FUNGI

(75) Inventors: Thomas Grote, Wachenheim (DE); Andreas Gypser, Mannheim (DE); Joachim Rheinheimer, Ludwigshafen (DE); Ingo Rose, Mannheim (DE); Peter Schäfer, Ottersheim (DE); Frank Schieweck, Heßheim (DE); Hubert Sauter, Mannheim (DE); Markus Gewehr, Kastellaun (DE); Bernd Müller, Frankenthal (DE); Jordi Tormo i Blasco, Limburgerhof (DE); Eberhard Ammermann, Heppenheim (DE); Siegfried Strathmann, Limburgerhof (DE); Gisela Lorenz, Hambach (DE); Reinhard Stierl, Mutterstadt (DE)

(73) Assignee: BASF SE, Ludwigshafen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 11/548,864

(22) Filed: Oct. 12, 2006

(65) Prior Publication Data
US 2007/0088026 A1    Apr. 19, 2007

Related U.S. Application Data

(62) Division of application No. 10/471,532, filed as application No. PCT/EP02/02739 on Mar. 13, 2002, now Pat. No. 7,153,860.

(30) Foreign Application Priority Data

Mar. 15, 2001 (DE) .................. 101 12 915
Apr. 2, 2001 (DE) .................. 101 16 432

(51) Int. Cl.
C07D 403/04 (2006.01)
C07D 239/38 (2006.01)
(52) U.S. Cl. .............. 544/315; 544/317; 544/330; 544/331
(58) Field of Classification Search ........... 544/315, 544/317, 330, 331
See application file for complete search history.

(56) References Cited

U.S. PATENT DOCUMENTS

| | | | |
|---|---|---|---|
| 3,479,357 A | 11/1969 | Wagner | 260/256.4 |
| 3,670,077 A | 6/1972 | Freeman et al. | 424/200 |
| 5,164,393 A | 11/1992 | Vermehren et al. | 514/256 |
| 5,250,530 A | 10/1993 | Giencke et al. | 514/256 |
| 5,739,333 A * | 4/1998 | Yamada et al. | 544/296 |
| 6,632,821 B2 * | 10/2003 | Pees et al. | 514/275 |
| 7,230,104 B2 * | 6/2007 | Pees et al. | 544/317 |

FOREIGN PATENT DOCUMENTS

| | | |
|---|---|---|
| BE | 518622 | 4/1953 |
| BE | 864399 | 6/1978 |
| CA | 2068328 | 5/1991 |
| EP | 0 251 083 | 1/1988 |
| WO | WO 01/96314 | 12/2001 |

OTHER PUBLICATIONS

Oehme et al., "Kristallin-flüssige 2-cyan-pyrimidine" (*Liquid-crystalline 2-cyano-pyrimidines*) Z. Chem. 17(2), pp. 63-69 (1977).

* cited by examiner

*Primary Examiner*—Deepak Rao
(74) *Attorney, Agent, or Firm*—Novak Druce + Quigg LLP

(57) ABSTRACT

5-Phenylpyrimidines of the formula I,

I in which the substituents have the following meanings:
$R^1$ is a five- to ten-membered saturated, partially unsaturated or aromatic mono- or bicyclic heterocycle comprising one to four hetero atoms selected from the group consisting of O, N or S, which heterocycle can be substituted as defined in the description,
$R^2$ is hydrogen, halogen, cyano, alkyl, haloalkyl or alkoxy;
$R^3$, $R^4$ are hydrogen, alkyl, haloalkyl, cycloalkyl, halocycloalkyl, alkenyl, haloalkenyl, cycloalkenyl, alkynyl, haloalkynyl or cycloalkynyl, $R^3$ and $R^4$ together with the nitrogen atom to which they are bonded may also form a five- or six-membered ring which can be interrupted by a hetero atom and have attached to it one or more substituents;
$R^5$, $R^6$ are hydrogen, halogen, alkyl, haloalkyl or alkoxy;
$R^7$, $R^8$ are hydrogen, halogen, alkyl or haloalkyl;
$R^9$ is hydrogen, halogen, alkyl, alkoxy, cycloalkoxy, haloalkoxy or alkoxycarbonyl, Processes and intermediates for the preparation of these compounds, and their use for controlling harmful fungi.

9 Claims, No Drawings

5-PHENYLPYRIMIDINES, THEIR PREPARATION, INTERMEDIATES FOR THEIR PREPARATION, AND THEIR USE FOR CONTROLLING HARMFUL FUNGI

This is a Divisional application of application Ser. No. 10/471,532, filed on Sep. 11, 2003 now U.S. Pat. No. 7,153,860, the entire disclosure of which is herewith incorporated by reference, which is a National Stage Application under 35 U.S.C. 371, based on International Application No. PCT/EP02/02739, filed Mar. 13, 2002, the entire disclosure of which is herewith incorporated by reference.

The present invention relates to 5-phenylpyrimidines of the formula I,

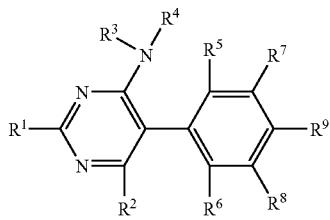

in which the substituents have the following meanings:

$R^1$ is a five- to ten-membered saturated, partially unsaturated or aromatic mono- or bicyclic heterocycle comprising one to four hetero atoms selected from the group consisting of O, N or S, except for pyridyl, it being possible for $R^1$ to be substituted by one to three identical or different groups $R^a$, $R^a$ is halogen, hydroxyl, cyano, oxo, nitro, amino, mercapto, $C_1$-$C_6$-alkyl, $C_1$-$C_6$-haloalkyl, $C_2$-$C_6$-alkenyl, $C_2$-$C_6$-alkynyl, $C_3$-$C_6$-cycloalkyl, $C_1$-$C_6$-alkoxy, $C_1$-$C_6$-haloalkoxy, carboxyl, $C_1$-$C_7$-alkoxycarbonyl, carbamoyl, $C_1$-$C_7$-alkylaminocarbonyl, $C_1$-$C_6$-alkyl-$C_1$-$C_6$-alkylaminocarbonyl, morpholinocarbonyl, pyrrolidinocarbonyl, $C_1$-$C_7$-alkylcarbonylamino, $C_1$-$C_6$-alkylamino, di($C_1$-$C_6$-alkyl)amino, $C_1$-$C_6$-alkylthio, $C_1$-$C_6$-alkylsulfinyl, $C_1$-$C_6$-alkylsulfonyl, hydroxysulfonyl, aminosulfonyl, $C_1$-$C_6$-alkylaminosulfonyl, di($C_1$-$C_6$-alkyl)aminosulfonyl;

$R^2$ is hydrogen, halogen, cyano, $C_1$-$C_6$-alkyl, $C_1$-$C_6$-haloalkyl, $C_1$-$C_6$-alkoxy, $C_1$-$C_4$-haloalkoxy or $C_3$-$C_6$-alkenyloxy;

$R^3$, $R^4$ independently of one another are hydrogen, $C_1$-$C_6$-alkyl, $C_1$-$C_6$-haloalkyl, $C_3$-$C_6$-cycloalkyl, $C_3$-$C_6$-halocycloalkyl, $C_2$-$C_6$-alkenyl, $C_2$-$C_6$-haloalkenyl, $C_3$-$C_6$-cycloalkenyl, $C_2$-$C_6$-alkynyl, $C_2$-$C_6$-haloalkynyl or $C_3$-$C_6$-acycloalkynyl, $R^3$ and $R^4$ may also, together with the nitrogen atom to which they are bonded, form a five- or six-membered ring which can be interrupted by a hetero atom selected from the group consisting of O, N and S and/or which can have attached to it one or more substituents selected from the group consisting of halogen, $C_1$-$C_6$-alkyl, $C_1$-$C_6$-haloalkyl and oxy-$C_1$-$C_3$-alkylenoxy or in which two adjacent C atoms or one N atom and one adjacent C atom can be linked by a $C_1$-$C_4$-alkylene chain;

$R^5$, $R^6$ independently of one another are hydrogen, halogen, $C_1$-$C_6$-alkyl, $C_1$-$C_6$-haloalkyl or $C_1$-$C_6$-alkoxy;

$R^7$, $R^8$ independently of one another are hydrogen, halogen, $C_1$-$C_6$-alkyl or $C_1$-$C_6$-haloalkyl;

$R^9$ is hydrogen, halogen, $C_1$-$C_6$-alkyl, $C_1$-$C_6$-alkoxy, $C_3$-$C_6$-cycloalkoxy, $C_1$-$C_6$-haloalkoxy, $C_1$-$C_6$-alkoxycarbonyl or $C_1$-$C_6$-alkylaminocarbonyl.

Moreover, the invention relates to processes and intermediates for the preparation of these compounds and to their use for controlling harmful fungi.

Fungicidally active 2-pyridyl-4-amino pyridine derivatives are disclosed in EP-A 407 899, pyridylpyrimidine derivatives are disclosed in DE-A 39 37 284, DE-A 39 37 285, DE-A 40 29 649, DE-A 40 34 762, DE-A 42 27 811, EP-A 481 405 and WO-A 92/10490.

The compounds described in the abovementioned publications are suitable as crop protection agents against harmful fungi.

In many cases, however, their action is not satisfactory. It is therefore an object of the present invention to provide compounds with an improved activity.

We have found that this object is achieved by the phenylpyrimidine derivatives I defined at the outset. Moreover, we have found processes and intermediates for their preparation and compositions comprising them for controlling harmful fungi, and their use.

The compounds of the formula I have an improved activity against harmful fungi compared with the known compounds.

The compounds I can be obtained via various routes. Compounds of the formula I in which $R^1$ is heterocycles bonded via nitrogen and $R^2$ is chlorine can be prepared, for example, by the following process:

The cyclocondensation of thiourea with alkyl phenylmalonates of the formula II gives compounds of the formula III

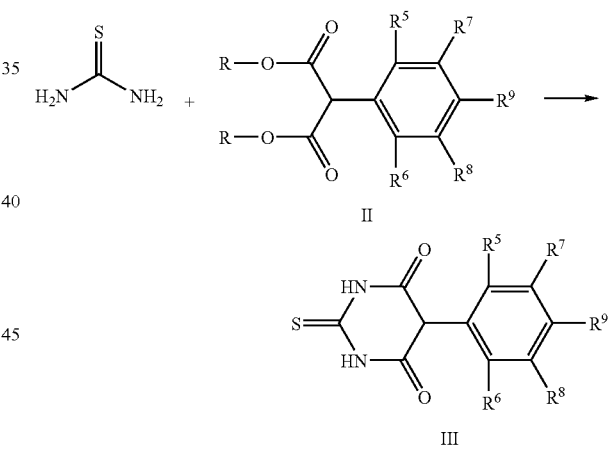

where, in formula II, R is $C_1$-$C_6$-alkyl. The reaction is usually carried out in a protic solvent such as, for example, alcohols, in particular ethanol. However, it may also be carried out in aprotic solvents such as, for example, pyridine, N,N-dimethylformamide, N,N-dimethylacetamide, or mixtures of these [cf. U.S. Pat. No. 4,331,590; Org. Prep. and Proced. Int., Vol. 10, pp. 21-27 (1978); Collect. Czech. Chem. Commun., Vol. 48, pp. 137-143 (1983); Heteroat. Chem., Vol. 10, pp. 17-23 (1999); Czech. Chem. Commun., Vol. 58, pp. 2215-2221 (1993).

It may be advantageous to carry out the process in the presence of a base, which may be employed in equimolar amounts or else in excess. Examples of suitable bases are alkali metal carbonates, alkaline earth metal carbonates, alkali metal hydrogen carbonates and alkaline earth metal hydrogen carbonates, for example the potassium and sodium salts, in particular $Na_2CO_3$ and $NaHCO_3$, or else nitrogen bases such as, for example, pyridine and tributylamine. The reaction temperature is normally 20-250° C., preferably 70-220° C.

The reactants are usually employed in an approximately stoichiometric ratio. However, it may be advantageous to employ thiourea in excess. The arylmalonates required are known (cf. EP-A 1002 788) or can be prepared by methods known from the literature.

Compounds III were reacted by means of alkylating agents IV to give the thiobarbituric acid derivatives. In formula IV, R is $C_1$-$C_6$-alkyl and X is a leaving group which can be eliminated nucleophilically. Formula IV generally represents customary alkylating agents such as $C_1$-$C_6$-alkyl halides, in particular methyl chloride and methyl bromide, di($C_1$-$C_6$-alkyl) sulfates, such as dimethyl sulfate, or a $C_1$-$C_6$-alkyl methanesulfonate, such as methyl methanesulfonate.

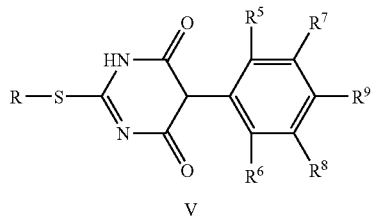

The reaction can be carried out in water or else in a dipolar aprotic solvent such as, for example, N,N-dimethylformamide [cf. U.S. Pat. No. 5,250,689], it is advantageously carried out in the presence of a base, which may be employed in equimolar amounts or else in excess. Suitable bases are alkali metal hydroxides, alkaline earth metal hydroxides, alkali metal hydrogen carbonates and alkaline earth metal hydrogen carbonates, such as, for example, KOH, NaOH, $NaHCO_3$ and $Na_2CO_3$, but also nitrogen bases such as pyridine. The reaction temperature is usually 0-100° C., preferably 10-60° C. The reactants are usually employed in an approximately stoichiometric ratio. However, it may be advantageous to employ the alkylating agent in excess.

Compounds V are converted into dichloropyrimidines of the formula VI [cf. U.S. Pat. No. 4,963,678; EP-A 745 593; DE-A 196 42 533; WO-A 99/32458; J. Org. Chem. Vol. 58, (1993), pp. 3785-3786; Helv. Chim. Acta, Vol. 64, (1981), pp. 113-152].

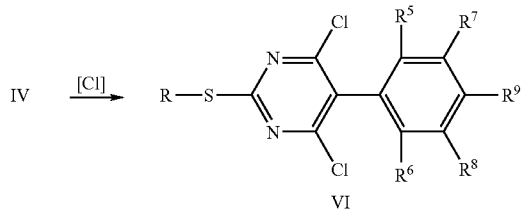

Examples of suitable chlorinating agents [Cl] are $POCl_3$, $PCl_3/Cl_2$ or $PCl_5$, or mixtures of these. The reaction can be carried out in an excess of chlorinating agent ($POCl_3$) or an inert solvent such as, for example, acetonitrile or 1,2-dichloroethane. Carrying out the reaction in $POCl_3$ is preferred.

This reaction is usually carried out at between 10 and 180° C. For practical reasons, the reaction temperature usually corresponds to the boiling point of the chlorinating agent employed ($POCl_3$) or of the solvent employed. The process is advantageously carried out with addition of N,N-dimethylformamide in catalytic or substoichiometric amounts or with addition of nitrogen bases such as, for example, N,N-dimethylaniline.

By amination with VII, the dichloro compounds of the formula VI are converted into the compounds of the formula VIII.

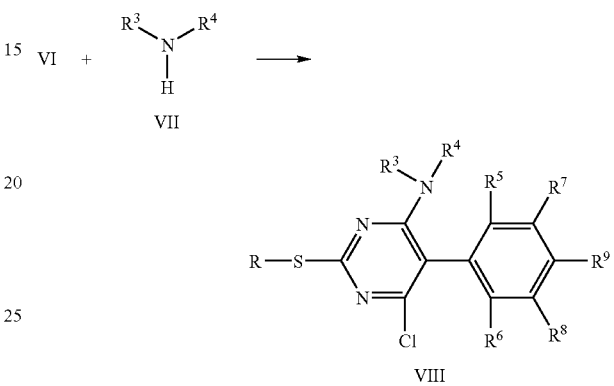

This reaction is usually carried out at from 0 to 150° C., preferably at from 20 to 120° C. [cf. J. Chem. Res. S (7), (1995), pp. 286-287, Liebigs Ann. Chem., (1995), pp. 1703-1705] in an inert solvent, if appropriate in the presence of an auxiliary base.

Suitable solvents are protic solvents, such as alcohols, for example ethanol, or aprotic solvents, such as aromatic hydrocarbons or ethers, for example toluene, o-, m- and p-xylene, diethyl ether, diisopropyl ether, tert-butyl methyl ether, dioxane or tetrahydrofuran, in particular tert-butyl methyl ether or tetrahydrofuran. Examples of suitable auxiliary bases are the following: $NaHCO_3$, $Na_2CO_3$, $Na_2HPO_4$, $Na_2B_4O_7$, diethylaniline or ethyldiisopropylamine.

The reactants are normally employed in an approximately stoichiometric ratio. However, it may be advantageous to employ the amine in excess.

The amines of the formula VII are commercially available or known from the literature or can be prepared by known methods.

The thio compounds VIII are oxidized to give the sulfones of the formula IX.

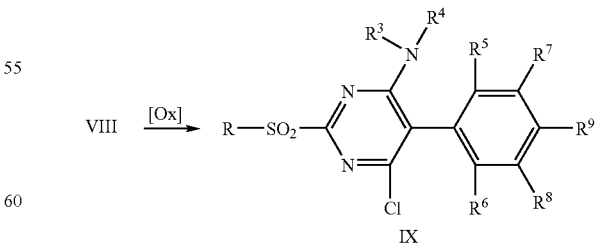

The reaction is usually carried out at from 0 to 100° C., preferably from 10 to 50° C., in the presence of protic or aprotic solvents [cf.: B. Kor. Chem. Soc., Vol. 16, (1995), pp. 489-492; Z. Chem., Vol. 17, (1977), p. 63].

Suitable solvents are alkylcarboxylic acids such as acetic acid or alcohols such as methanol, water or halogenated hydrocarbons such as dichloromethane or chloroform. Mixtures of these may also be employed. Preferred are acetic acid and a methanol/water mixture.

Examples of suitable oxidants are hydrogen peroxide, pertungstic acid, peracetic acid, 3-chloroperbenzoic acid, perphthalic acid, chlorine, oxygen and Oxone® ($KHSO_5$). The oxidant is usually employed in an approximately stoichiometric ratio. However, it may be advantageous to carry out the process with an excess of oxidant.

Pyrimidine derivatives of the formula IX are converted into the compounds I by reaction with heterocycles of the formula X. In formula X, the cycle A is a five- to ten-membered saturated, partially unsaturated or aromatic nitrogen-containing ring.

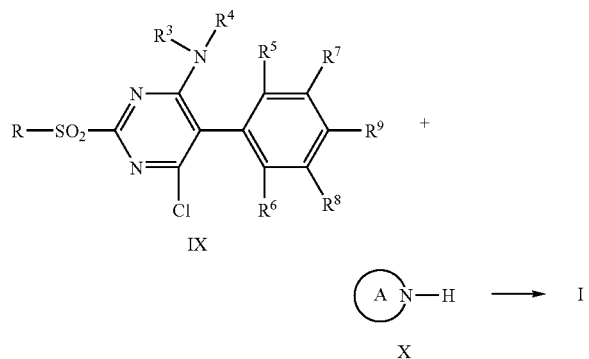

This reaction is usually carried out at from 0 to 200° C., preferably at from 10 to 150° C., in the presence of a dipolar aprotic solvent such as N,N-dimethylformamide, tetrahydrofuran or acetonitrile [cf. DE-A 39 01 084; Chimia, Vol. 50, (1996), pp. 525-530; Khim. Geterotsikl. Soedin, Vol. 12, (1998), pp. 1696-1697].

The reactants are usually employed in an approximately stoichiometric ratio. However, it may be advantageous to employ the nitrogen heterocycle of the formula X in excess.

The reaction is usually carried out in the presence of a base, which may be employed in equimolar amounts or else in excess. Suitable bases are alkali metal carbonates and alkali metal halogen carbonates, for example $Na_2CO_3$ and $NaHCO_3$, nitrogen bases such as triethylamine, tributylamine and pyridine, alkali metal alkoxides such as sodium ethoxide or potassium tert-butoxide, alkali metal amides such as $NaNH_2$, or else alkali metal hydrides such as LiH or NaH.

Compounds of the formula I in which $R^1$ is bonded to the pyrimidine ring via a carbon atom can be synthesized for example as follows:

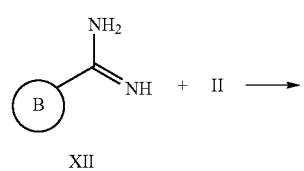

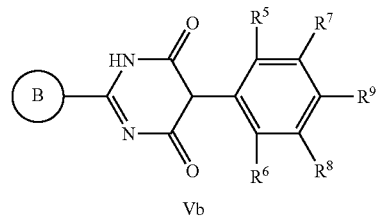

In formulae Vb and XII, the cycle B is a five- to ten-membered saturated, partially unsaturated or aromatic heterocycle ring which is bonded via carbon.

The reaction is usually carried out at from 50 to 250° C., preferably at from 100 to 200° C. in the presence of a inert solvent [cf.: Austr. J. Chem., Vol. 32, (1979), pp. 669-679; J. Org. Chem., Vol. 58, (1993), pp. 3785-3786; Arm. Xim. ZH, Vol. 38, N11, (1985), 718-719].

The following are suitable as solvents: protic solvents such as alcohols, preferably methanol or ethanol, or aprotic solvents such as tributylamine or ethylene glycol dimethyl ether.

As a rule, it is advantageous to carry out the process in the presence of a base, which can be employed in equimolar amounts or else in excess. Suitable bases are alkali metal alkoxides and alkaline earth metal alkoxides such as sodium methoxide, sodium ethoxide, potassium ethoxide, potassium tert-butoxide, in particular sodium methoxide, or else nitrogen bases such as triethylamine, triisopropylethylamine and N-methylpiperidine, in particular pyridine and tributylamine.

Usually, the reactants are employed in approximately stoichiometric amounts. However, it may also be advantageous to employ one of the reactants in excess.

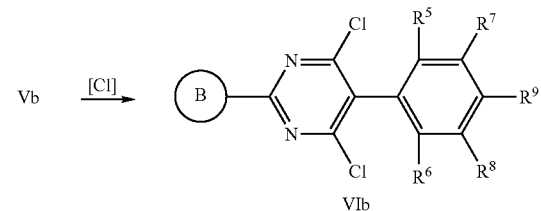

The chlorination of Vb to give VIb is carried out under the same conditions as the chlorination of V to give VI.

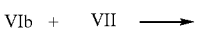

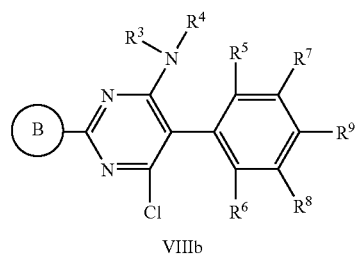

The amination of the dichloropyrimidine VIb with VII is carried out under the same conditions as the amination of VI to give VIII.

Compounds of the formula VI in which $R^2$ is alkoxy are obtained from the corresponding chloro compounds of the formula VI (R²=Cl) by reaction with alkali metal alkoxides or alkaline earth metal alkoxides [cf.: Heterocycles, Vol. 32, (1991), pp. 1327-1340; J. Heterocycl. Chem. Vol. 19, (1982), pp. 1565-1567; Geterotsikl. Soedin, (1991) pp. 400-402].

Compounds of the formula I in which R² is cyano are obtained from the corresponding chloro compounds of the formula VI (R²=Cl) by reaction with alkali metal cyanides, alkaline earth metal cyanides or metal cyanides, such as NaCN, KCN or Zn(CN)$_2$, [cf.: Heterocycles, Vol. 39, (1994), pp. 345-356; Collect. Czech. Chem. Commun. Vol. 60, (1995), pp. 1386-1389; Acta Chim. Scand., Vol. 50, (1996), pp. 58-63].

Compounds of the formula I in which R² is hydrogen are obtained from the corresponding chloro compounds of the formula VI (R²=Cl) by catalytic hydrogenation [cf.: J. Fluorine Chem. Vol. 45, (1989), pp. 417-430; J. Heterocycl. Chem. Vol. 29, (1992), pp. 1369-1370], or by reduction with zinc in acetic acid [cf.: Org. Prep. Proced. Int., Vol. 27, (1995), pp. 600-602; JP-A 09/165 379].

Compounds of the formula I in which R² is $C_1$-$C_6$-alkyl or $C_1$-$C_6$-haloalkyl can be prepared in analogy to the above-described synthesis sequence to give the compounds I in which R² is chlorine by suitably altering the starting materials of the formula II. Instead of the phenylmalonates of the formula II, phenyl-β-ketoesters of the formula XIII in which R² is alkyl are reacted with thiourea or the amidine of the formula XII. The reactions which follow are carried out analogously to the compounds where R²=chlorine.

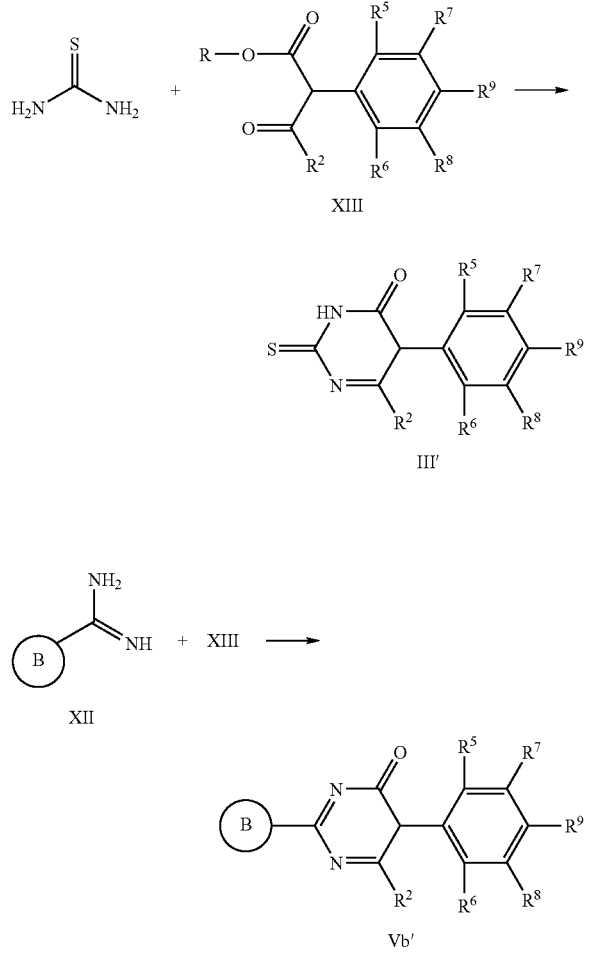

The reaction mixtures are worked up in the customary fashion, for example by mixing with water, separating the phases and, if appropriate, chromatographic purification of the crude products. Some of the intermediates and end products are obtained in the form of colorless or pale brown viscous oils, which are freed or purified from volatile constituents under reduced pressure and at moderately elevated temperature. If the intermediates and end products are obtained as solids, they may also be purified by recrystallization or digestion.

If individual compounds I cannot be obtained via the above-described routes, they can be prepared by derivatizing other compounds I.

In the definitions of the symbols given for the above formulae, collective terms were used which generally represent the following substituents:

Halogen: fluorine, chlorine, bromine and iodine;

Alkyl: saturated, straight-chain or branched hydrocarbon radicals having 1 to 4, 6 or 8 carbon atoms, for example $C_1$-$C_6$-alkyl such as methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl;

Haloalkyl: straight-chain or branched alkyl groups having 1 to 8 carbon atoms (as mentioned above), it being possible for some or all of the hydrogen atoms in these groups to be replaced by halogen atoms as mentioned above, for example $C_1$-$C_2$-haloalkyl such as chloromethyl, bromomethyl, dichloromethyl, trichloromethyl, fluoromethyl, difluoromethyl, trifluoromethyl, chlorfluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl and 1,1,1-trifluoroprop-2-yl;

Alkenyl: unsaturated, straight-chain or branched hydrocarbon radicals having 2 to 4, 6 or 8 carbon atoms and a double bond in any position, for example $C_2$-$C_6$-alkenyl such as ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl;

Alkynyl: straight-chain or branched hydrocarbon groups having 2 to 4, 6 or 8 carbon atoms and a triple bond in any position, for example $C_2$-$C_6$-alkynyl such as ethynyl, 1-propynyl, 2-propynyl, 1-butynyl, 2-butynyl, 3-butynyl, 1-methyl-2-propynyl, 1-pentynyl, 2-pentynyl, 3-pentynyl, 4-pentynyl, 1-methyl-2-butynyl, 1-methyl-3-butynyl, 2-methyl-3-butynyl, 3-methyl-1-butynyl, 1,1-dimethyl-2-propynyl, 1-ethyl-2-propynyl, 1-hexynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-1-pentynyl, 3-methyl-4-pentynyl, 4-methyl-1-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 3,3-dimethyl-1-butynyl, 1-ethyl-2-butynyl, 1-ethyl-3-butynyl, 2-ethyl-3-butynyl und 1-ethyl-1-methyl-2-propynyl;

Cycloalkyl: monocyclic, saturated hydrocarbon groups having 3 to 6 carbon ring members such as cyclopropyl, cyclobutyl, cyclopentyl and cyclohexyl;

Alkoxycarbonyl: an alkoxy group having 1 to 6 carbon atoms (as mentioned above) which is bonded to the skeleton via a carbonyl group (—CO—);

Oxyalkylenoxy: divalent unbranched chains of 1 to 3 $CH_2$ groups, both valencies being bonded to the skeleton via an oxygen atom, for example $OCH_2O$, $OCH_2CH_2O$ and $OCH_2CH_2CH_2O$;

five- to ten-membered saturated or partially unsaturated heterocycle containing one to four hetero atoms selected from the group consisting of oxygen, nitrogen or sulfur: mono- or bicyclic heterocycles (heterocyclyl) containing, in addition to carbon ring members, one to three nitrogen atoms and/or one oxygen or sulfur atom or one or two oxygen and/or sulfur atoms, for example 2-tetrahydrofuranyl, 3-tetrahydrofuranyl, 2-tetrahydrothienyl, 3-tetrahydrothienyl, 2-pyrrolidyinyl, 3-pyrrolidinyl, 3-isoxazolidinyl, 4-isoxazolidinyl, 5-isoxazolidinyl, 3-isothiazolidinyl, 4-isothiazolidinyl, 5-isothiazolidinyl, 3-pyrazolidinyl, 4-pyrazolidinyl, 5-pyrazolidinyl, 2-oxazolidinyl, 4-oxazolidinyl, 5-oxazolidinyl, 2-thiazolidinyl, 4-thiazolidinyl, 5-thiazolidinyl, 2-imidazolidinyl, 4-imidazolidinyl, 1,2,4-oxadiazolidin-3-yl, 1,2,4-oxadiazolidin-5-yl, 1,2,4-thiadiazolidin-3-yl, 1,2,4-thiadiazolidin-5-yl, 1,2,4-triazolidin-3-yl, 1,3,4-oxadiazolidin-2-yl, 1,3,4-thiadiazolidin-2-yl, 1,3,4-triazolidin-2-yl, 2,3-dihydrofur-2-yl, 2,3-dihydrofur-3-yl, 2,4-dihydrofur-2-yl, 2,4-dihydrofur-3-yl, 2,3-dihydrothien-2-yl, 2,3-dihydrothien-3-yl, 2,4-dihydrothien-2-yl, 2,4-dihydrothien-3-yl, 2-pyrrolin-2-yl, 2-pyrrolin-3-yl, 3-pyrrolin-2-yl, 3-pyrrolin-3-yl, 2-isoxazolin-3-yl, 3-isoxazolin-3-yl, 4-isoxazolin-3-yl, 2-isoxazolin-4-yl, 3-isoxazolin-4-yl, 4-isoxazolin-4-yl, 2-isoxazolin-5-yl, 3-isoxazolin-5-yl, 4-isoxazolin-5-yl, 2-isothiazolin-3-yl, 3-isothiazolin-3-yl, 4-isothiazolin-3-yl, 2-isothiazolin-4-yl, 3-isothiazolin-4-yl, 4-isothiazolin-4-yl, 2-isothiazolin-5-yl, 3-isothiazolin-5-yl, 4-isothiazolin-5-yl, 2,3-dihydropyrazol-1-yl, 2,3-dihydropyrazol-2-yl, 2,3-dihydropyrazol-3-yl, 2,3-dihydropyrazol-4-yl, 2,3-dihydropyrazol-5-yl, 3,4-dihydropyrazol-1-yl, 3,4-dihydropyrazol-3-yl, 3,4-dihydropyrazol-4-yl, 3,4-dihydropyrazol-5-yl, 4,5-dihydropyrazol-1-yl, 4,5-dihydropyrazol-3-yl, 4,5-dihydropyrazol-4-yl, 4,5-dihydropyrazol-5-yl, 2,3-dihydrooxazol-2-yl, 2,3-dihydrooxazol-3-yl, 2,3-dihydrooxazol-4-yl, 2,3-dihydrooxazol-5-yl, 3,4-dihydrooxazol-2-yl, 3,4-dihydrooxazol-3-yl, 3,4-dihydrooxazol-4-yl, 3,4-dihydrooxazol-5-yl, 3,4-dihydrooxazol-2-yl, 3,4-dihydrooxazol-3-yl, 3,4-dihydrooxazol-4-yl, 2-piperidinyl, 3-piperidinyl, 4-piperidinyl, 1,3-dioxan-5-yl, 2-tetrahydropyranyl, 4-tetrahydropyranyl, 2-tetrahydrothienyl, 3-hexahydropyridazinyl, 4-hexahydropyridazinyl, 2-hexahydropyrimidinyl, 4-hexahydropyrimidinyl, 5-hexahydropyrimidinyl, 2-piperazinyl, 1,3,5-hexahydrotriazin-2-yl and 1,2,4-hexahydrotriazin-3-yl;

five- to ten-membered aromatic heterocycle containing one to four hetero atoms selected from the group consisting of oxygen, nitrogen or sulfur: mononuclear or binuclear heteroaryl, for example 5-membered heteroaryl containing one to four nitrogen atoms or one to three nitrogen atoms and one sulfur or oxygen atom: 5-membered heteroaryl ring groups which, in addition to carbon atoms, may contain one to four nitrogen atoms or one to three nitrogen atoms and one sulfur or oxygen atom as ring members, for example 2-furyl, 3-furyl, 2-thienyl, 3-thienyl, 2-pyrrolyl, 3-pyrrolyl, 3-isoxazolyl, 4-isoxazolyl, 5-isoxazolyl, 3-isothiazolyl, 4-isothiazolyl, 5-isothiazolyl, 3-pyrazolyl, 4-pyrazolyl, 5-pyrazolyl, 2-oxazolyl, 4-oxazolyl, 5-oxazolyl, 2-thiazolyl, 4-thiazolyl, 5-thiazolyl, 2-imidazolyl, 4-imidazolyl, 1,2,4-oxadiazol-3-yl, 1,2,4-oxadiazol-5-yl, 1,2,4-thiadiazol-3-yl, 1,2,4-thiadiazol-5-yl, 1,2,4-triazol-3-yl, 1,3,4-oxadiazol-2-yl, 1,3,4-thiadiazol-2-yl und 1,3,4-triazol-2-yl;

benzo-fused 5-membered heteroaryl containing one to three nitrogen atoms or one nitrogen atom and one oxygen or sulfur atom: 5-membered heteroaryl ring groups which, in addition to carbon atoms, may contain one to four nitrogen atoms or one to three nitrogen atoms and one sulfur or oxygen atom as ring members and in which two adjacent carbon ring members or one nitrogen and one adjacent carbon ring member may be bridged by a buta-1,3-dien-1,4-diyl group in which one or two C atoms can be replaced by N atoms;

5-membered heteroaryl which is bonded via nitrogen and which contains one to four nitrogen atoms, or benzo-fused 5-membered heteroaryl which is bonded via nitrogen and contains one to three nitrogen atoms: 5-membered heteroaryl ring groups which, in addition to carbon atoms, may contain one to four nitrogen atoms or one to three nitrogen atoms as ring members and in which two adjacent carbon ring members or one nitrogen and one adjacent carbon ring member may be bridged by a buta-1,3-dien-1,4-diyl group, in which one or two C atoms can be replaced by N atoms, these rings being bonded to the skeleton via one of the nitrogen ring members;

6-membered heteroaryl containing one to three, or one to four, nitrogen atoms: 6-membered heteroaryl ring groups which, in addition to carbon atoms, may contain one to three, or one to four, nitrogen atoms as ring members, for example 3-pyridazinyl, 4-pyridazinyl, 2-pyrimidinyl, 4-pyrimidinyl, 5-pyrimidinyl, 2-pyrazinyl, 1,3,5-triazin-2-yl and 1,2,4-triazin-3-yl;

The especially preferred embodiments of the intermediates with regard to the variables correspond to those of radicals $R^1$ to $R^9$ of the formula I.

With regard to the intended use of the phenylpyrimidines of the formula I, the following meanings of the substituents are especially preferred, in each case alone or in combination:

Preferred compounds I are those in which $R^1$ is an aromatic heterocycle.

Furthermore preferred compounds I are those in which $R^1$ is a five- to six-membered, in particular a five-membered, heterocycle.

Particularly preferred compounds of the formula I are those in which $R^1$ is a nitrogen-containing heterocycle.

In addition, preferred compounds I are those in which $R^1$ is a heterocycle which is bonded to the pyrimidine ring via nitrogen.

Equally preferred are compounds I in which $R^1$ is one of the following groups: pyrrolyl, pyrazolyl, imidazolyl, 1,2,4-triazolyl, 1,2,3-triazolyl, tetrazolyl, 1,2,3-triazinyl, 1,2,4-triazinyl, oxazolyl, isoxazolyl, 1,3,4-oxadiazolyl, furanyl, thiophenyl, thiazolyl, isothiazolyl, it being possible for the heterocycle to be bonded to the pyrimidine ring via C or N.

Preferred compounds I are furthermore those in which the cycle $R^1$ is pyridazinyl, pyrimidinyl or pyrazinyl, in particular 2-pyrimidinyl.

Equally preferred compounds I are those in which $R^1$ is pyrazolyl, pyrrolyl, imidazolyl, 1,2,3-triazolyl, 1,2,4-triazolyl, tetrazolyl, 2-pyridinyl, 2-pyrimidinyl, pyrazinyl or 3-pyridazinyl, each of which is optionally substituted by up to three groups $R^a$ or $R^{a'}$.

Especially preferred compounds I are those in which an $R^1$ is pyrazolyl, 1,2,3-triazolyl or 1,2,4-triazolyl, in particular 1-pyrazolyl.

In addition, especially preferred compounds I are those in which the cycle $R^1$ is substituted by one to three identical or different groups $R^{a'}$ from among those which follow:

halogen, hydroxyl, cyano, nitro, amino, mercapto, $C_1$-$C_6$-alkyl, $C_1$-$C_6$-haloalkyl, $C_2$-$C_6$-alkenyl, $C_2$-$C_6$-alkynyl, $C_3$-$C_6$-cycloalkyl, $C_1$-$C_6$-alkoxy, $C_1$-$C_6$-haloalkoxy, carboxyl, $C_1$-$C_7$-alkoxycarbonyl, carbamoyl, $C_1$-$C_7$-alkylaminocarbonyl, $C_1$-$C_6$-alkyl-$C_1$-$C_6$-alkylaminocarbonyl, morpholinocarbonyl, pyrrolidinocarbonyl, $C_1$-$C_7$-alkylcarbonylamino, $C_1$-$C_6$-alkylamino, di($C_1$-$C_6$-alkyl)amino, $C_1$-$C_6$-alkylthio, $C_1$-$C_6$-alkylsulfinyl, $C_1$-$C_6$-alkylsulfonyl, hydroxysulfonyl, aminosulfonyl, $C_1$-$C_6$-alkylaminosulfonyl or di($C_1$-$C_6$-alkyl)aminosulfonyl.

Especially preferred compounds I are, in particular, those in which the cycle $R^1$ is substituted by one to three identical or different groups $R^{a''}$ from amongst those which follow:

halogen, cyano, nitro, amino, $C_1$-$C_6$-alkyl, $C_1$-$C_6$-haloalkyl, $C_1$-$C_6$-alkoxy, carboxyl, $C_1$-$C_7$-alkoxycarbonyl, carbamoyl, $C_1$-$C_7$-alkylaminocarbonyl, di($C_1$-$C_6$-alkyl)aminocarbonyl or $C_1$-$C_7$-alkylcarbonylamino.

Especially preferred compounds I are those in which $R^1$ is unsubstituted or monosubstituted by halogen, cyano, nitro, methyl or methoxy.

Equally preferred compounds I are those in which $R^2$ is other than hydrogen.

Moreover, especially preferred compounds I are those in which $R^2$ is halogen, $C_1$-$C_6$-alkyl or $C_1$-$C_6$-alkoxy, in particular halogen.

Especially preferred compounds of the formula I are those in which $R^2$ is chlorine.

Moreover, preferred compounds of the formula I are those in which $R^3$ is hydrogen.

Equally especially preferred compounds I are those in which $R^3$ and $R^4$ independently of one another are $C_1$-$C_6$-alkyl, $C_1$-$C_6$-haloalkyl, $C_3$-$C_6$-cycloalkyl, $C_2$-$C_6$-alkenyl.

Particularly preferred compounds I are those in which $R^3$ is hydrogen and $R^4$ is $C_1$-$C_4$-halogenalkyl.

Furthermore, preferred compounds I are those in which $R^3$ and $R^4$ together with the nitrogen atom to which they are bonded form a five- or six-membered ring which can be interrupted by an oxygen atom and can have attached to it one or two $C_1$-$C_6$-alkyl substituents.

Furthermore, preferred compounds I are also those in which not both $R^5$ and $R^6$ are hydrogen.

Especially preferred compounds I are those in which $R^5$ is hydrogen.

Equally, especially preferred compounds I are those in which $R^5$ is hydrogen and $R^6$ is halogen or methyl.

Compounds of the formula I which are especially preferred are furthermore those in which $R^7$ and $R^8$ are identical or different and are hydrogen or halogen.

Moreover, especially preferred compounds I are those in which $R^9$ is hydrogen, halogen or $C_1$-$C_4$-alkoxy.

Equally, compounds I' in which $R^1$ to $R^4$ are as defined for formula I and $R^A$ is one of the following combinations of radicals: 2-chloro,6-fluoro; 2,6-difluoro; 2,6-dichloro; 2-methyl,4-fluoro; 2-methyl,6-fluoro; 2-fluoro,4-methyl; 2,4,6-trifluoro; 2,6-difluoro, 4-methoxy, 2,4-dimethyl and pentafluoro are especially preferred.

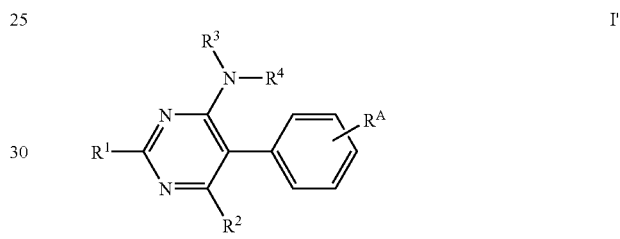

I'

In addition, compounds of the formula I' which are especially preferred are those in which $R^A$ is 2,4,6-trifluoro.

Particularly preferred with regard to their use are the compounds I compiled in the tables which follow. In the tables, the groups mentioned for a substituent additionally constitute an especially preferred embodiment of the substituent in question per se, independently of the combination in which they are mentioned.

Table 1

Compounds of the formula I-1 in which $R^5$ is fluorine, $R^6$ is chlorine and $R^7$, $R^8$ and $R^9$ are hydrogen and, for each compound, the combination of the radicals $R^3$ and $R^4$ corresponds to one line of Table A

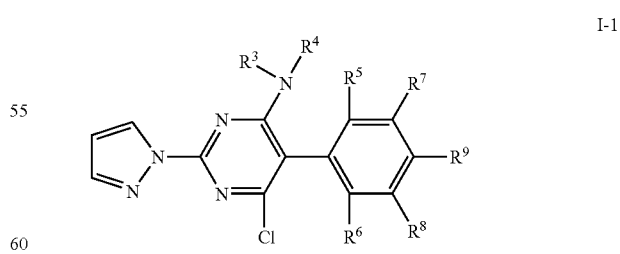

I-1

Table 2

Compounds of the formula I-1 in which $R^5$ and $R^6$ are fluorine, and $R^7$, $R^8$ and $R^9$ are hydrogen and, for each compound, the combination of the radicals $R^3$ and $R^4$ corresponds to one line of Table A Table 3
Compounds of the formula I-1 in which $R^5$ and $R^6$ are chlorine and $R^7$, $R^8$ and $R^9$ are hydrogen and, for each compound, the combination of the radicals $R^3$ and $R^3$ corresponds to one line of Table A Table 4
Compounds of the formula I-1 in which $R^5$ is fluorine, $R^6$ is methyl and $R^7$, $R^8$ and $R^9$ are hydrogen and, for each compound, the combination of the radicals $R^3$ and $R^4$ corresponds to one line of Table A Table 5
Compounds of the formula I-1 in which $R^5$, $R^6$ and $R^9$ are fluorine and $R^7$ and $R^8$ are hydrogen and, for each compound, the combination of the radicals $R^3$ and $R^4$ corresponds to one line of Table A Table 6
Compound of the formula I-1 in which $R^5$ and $R^6$ are fluorine, $R^7$ and $R^8$ are hydrogen and $R^9$ is methoxy and, for each compound, the combination of the radicals $R^3$ and $R^4$ corresponds to one line of Table A Table 7
Compounds of the formula I-1 in which $R^5$, $R^6$, $R^7$, $R^8$ and $R^9$ are fluorine and, for each compound, the combination of the radicals $R^3$ and $R^4$ corresponds to one line of Table A Table 8
Compounds of the formula I-1 in which $R^5$ is methyl, $R^6$, $R^7$ and $R^8$ are hydrogen and $R^9$ are fluorine and, for each compound, the combination of the radicals $R^3$ and $R^4$ corresponds to one line of Table A Table 9
Compounds of the formula I-1 in which $R^5$ is fluorine, $R^6$, $R^7$ and $R^8$ are hydrogen and $R^9$ are methyl and, for each compound, the combination of the radicals $R^3$ and $R^4$ corresponds to one line of Table A Table 10
Compounds of the formula I-1 in which $R^5$ and $R^9$ are methyl and $R^6$, $R^7$ and $R^8$ are hydrogen and, for each compound, the combination of the radicals $R^3$ and $R^4$ corresponds to one line of Table A Table 11
Compounds of the formula I-2 in which $R^5$ is fluorine, $R^6$ is chlorine and $R^7$, $R^8$ and $R^9$ are hydrogen and, for each compound, the combination of the radicals $R^3$ and $R^4$ corresponds to one line of Table A Table 13
Compounds of the formula I-2 in which $R^5$ and $R^6$ are chlorine and $R^7$, $R^8$ and $R^9$ are hydrogen and, for each compound, the combination of the radicals $R^3$ and $R^4$ corresponds to one line of Table A Table 14
Compounds of the formula I-2 in which $R^5$ is fluorine and $R^6$ is methyl and $R^7$, $R^8$ and $R^9$ are hydrogen and, for each compound, the combination of the radicals $R^3$ and $R^4$ corresponds to one line of Table A Table 15
Compounds of the formula I-2 in which $R^5$, $R^6$ and $R^9$ are fluorine and $R^7$ and $R^8$ are hydrogen and, for each compound, the combination of the radicals $R^3$ and $R^4$ corresponds to one line of Table A Table 16
Compounds of the formula I-2 in which $R^5$ and $R^6$ are fluorine, $R^7$ and $R^8$ are hydrogen and $R^9$ is methoxy and, for each compound, the combination of the radicals $R^3$ and $R^4$ corresponds to one line of Table A Table 17
Compounds of the formula I-2 in which $R^5$, $R^6$, $R^7$, $R^8$ and $R^9$ are fluorine and, for each compound, the combination of the radicals $R^3$ and $R^4$ corresponds to one line of Table A Table 18
Compounds of the formula I-2 in which $R^5$ is methyl, $R^6$, $R^7$ and $R^8$ is hydrogen and $R^9$ is fluorine and, for each compound, the combination of the radicals $R^3$ and $R^4$ corresponds to one line of Table A Table 19
Compounds of the formula I-2 in which $R^5$ is fluorine, $R^6$, $R^7$ and $R^8$ are hydrogen and $R^9$ is methyl and, for each compound, the combination of the radicals $R^3$ and $R^4$ corresponds to one line of Table A Table 20
Compounds of the formula I-2 in which $R^5$ and $R^9$ are methyl and $R^6$, $R^7$ and $R^8$ are hydrogen and, for each compound, the combination of the radicals $R^3$ and $R^4$ corresponds to one line of Table A Table 21
Compounds of the formula I-3 in which $R^5$ is fluorine, $R^6$ is chlorine and $R^7$, $R^8$ and $R^9$ are hydrogen and, for each compound, the combination of the radicals $R^3$ and $R^4$ corresponds to one line of Table A

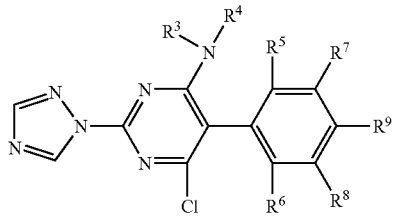

I-2

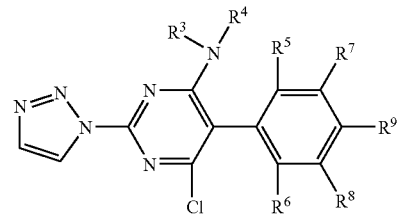

I-3

Table 12
Compounds of the formula I-2 in which $R^5$ and $R^6$ are fluorine and $R^7$, $R^8$ and $R^9$ are hydrogen and, for each compound, the combination of the radicals $R^3$ and $R^4$ corresponds to one line of Table A Table 22
Compounds of the formula I-3 in which $R^5$ and $R^6$ are fluorine and $R^7$, $R^8$ and $R^9$ are hydrogen and, for each compound, the combination of the radicals $R^3$ and $R^4$ corresponds to one line of Table A Table 23
Compounds of the formula I-3 in which $R^5$ and $R^6$ are chlorine and $R^7$, $R^8$ and $R^9$ are hydrogen and, for each compound, the combination of the radicals $R^3$ and $R^4$ corresponds to one line of Table A Table 24
Compounds of the formula I-3 in which $R^5$ is fluorine and $R^6$ is methyl and $R^7$, $R^8$ and $R^9$ are hydrogen and, for each compound, the combination of the radicals $R^3$ and $R^4$ corresponds to one line of Table A Table 25
Compounds of the formula I-3 in which $R^5$, $R^6$ and $R^9$ are fluorine and $R^7$ and $R^8$ are hydrogen and, for each compound, the combination of the radicals $R^3$ and $R^4$ corresponds to one line of Table A Table 26
Compounds of the formula I-3 in which $R^5$ and $R^6$ are fluorine, $R^7$ and $R^8$ are hydrogen and $R^9$ is methoxy and, for each compound, the combination of the radicals $R^3$ and $R^4$ corresponds to one line of Table A Table 27
Compounds of the formula I-3 in which $R^5$, $R^6$, $R^7$, $R^8$ and $R^9$ are fluorine and, for each compound, the combination of the radicals $R^3$ and $R^4$ corresponds to one line of Table A Table 28
Compounds of the formula I-3 in which $R^5$ is methyl, $R^6$, $R^7$ and $R^8$ is hydrogen and $R^9$ is fluorine and, for each compound, the combination of the radicals $R^3$ and $R^4$ corresponds to one line of Table A Table 29
Compounds of the formula I-3 in which $R^5$ is fluorine, $R^6$, $R^7$ and $R^8$ is hydrogen and $R^9$ is methyl and, for each compound, the combination of the radicals $R^3$ and $R^4$ corresponds to one line of Table A Table 30
Compounds of the formula I-3 in which $R^5$ and $R^9$ are methyl and $R^6$, $R^7$ and $R^8$ are hydrogen and, for each compound, the combination of the radicals $R^3$ and $R^4$ corresponds to one line of Table A Table 31
Compounds of the formula I-4 in which $R^5$ is fluorine, $R^6$ is chlorine and $R^7$, $R^8$ and $R^9$ are hydrogen and, for each compound, the combination of the radicals $R^3$ and $R^4$ corresponds to one line of Table A

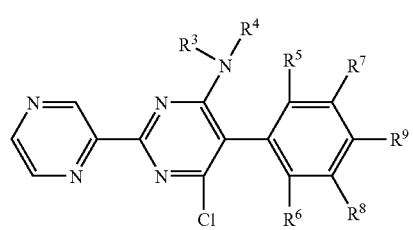

I-4

Table 32
Compounds of the formula I-4 in which $R^5$ and $R^6$ are fluorine and $R^7$, $R^8$ and $R^9$ are hydrogen and, for each compound, the combination of the radicals $R^3$ and $R^4$ corresponds to one line of Table A Table 33
Compounds of the formula I-4 in which $R^5$ and $R^6$ are chlorine and $R^7$, $R^8$ and $R^9$ are hydrogen and, for each compound, the combination of the radicals $R^3$ and $R^4$ corresponds to one line of Table A Table 34
Compounds of the formula I-4 in which $R^5$ is fluorine and $R^6$ is methyl and $R^7$, $R^8$ and $R^9$ are hydrogen and, for each compound, the combination of the radicals $R^3$ and $R^4$ corresponds to one line of Table A Table 35
Compounds of the formula I-4 in which $R^5$, $R^6$ and $R^9$ are fluorine and $R^7$ and $R^8$ are hydrogen and, for each compound, the combination of the radicals $R^3$ and $R^4$ corresponds to one line of Table A Table 36
Compounds of the formula I-4 in which $R^5$ and $R^6$ are fluorine, $R^7$ and $R^8$ are hydrogen and $R^9$ is methoxy and, for each compound, the combination of the radicals $R^3$ and $R^4$ corresponds to one line of Table A Table 37
Compounds of the formula I-4 in which $R^5$, $R^6$, $R^7$, $R^8$ and $R^9$ are fluorine and, for each compound, the combination of the radicals $R^3$ and $R^4$ corresponds to one line of Table A Table 38
Compounds of the formula I-4 in which $R^5$ is methyl, $R^6$, $R^7$ and $R^8$ are hydrogen and $R^9$ is fluorine and, for each compound, the combination of the radicals $R^3$ and $R^4$ corresponds to one line of Table A Table 39
Compounds of the formula I-4 in which $R^5$ is fluorine, $R^6$, $R^7$ and $R^8$ are hydrogen and $R^9$ is methyl and, for each compound, the combination of the radicals $R^3$ and $R^4$ corresponds to one line of Table A Table 40
Compounds of the formula I-4 in which $R^5$ and $R^9$ are methyl and $R^6$, $R^7$ and $R^8$ are hydrogen and, for each compound, the combination of the radicals $R^3$ and $R^4$ corresponds to one line of Table A

TABLE A

| No. | $R^3$ | $R^4$ |
|---|---|---|
| A-1 | $CH_2CH_3$ | H |
| A-2 | $CH_2CH_3$ | $CH_3$ |
| A-3 | $CH_2CH_3$ | $CH_2CH_3$ |
| A-4 | $CH_2CH_2CH_3$ | H |
| A-5 | $CH_2CH_2CH_3$ | $CH_3$ |
| A-6 | $CH_2CH_2CH_3$ | $CH_2CH_3$ |
| A-7 | $CH_2CH_2CH_3$ | $CH_2CH_2CH_3$ |
| A-8 | $CH_2CH_2F$ | H |
| A-9 | $CH_2CH_2F$ | $CH_3$ |
| A-10 | $CH_2CH_2F$ | $CH_2CH_3$ |
| A-11 | $CH_2CF_3$ | H |
| A-12 | $CH_2CF_3$ | $CH_3$ |
| A-13 | $CH_2CF_3$ | $CH_2CH_3$ |
| A-14 | $CH_2CF_3$ | $CH_2CH_2CH_3$ |
| A-15 | $CH_2CCl_3$ | H |
| A-16 | $CH_2CCl_3$ | $CH_3$ |
| A-17 | $CH_2CCl_3$ | $CH_2CH_3$ |
| A-18 | $CH_2CCl_3$ | $CH_2CH_2CH_3$ |
| A-19 | $CH(CH_3)_2$ | H |
| A-20 | $CH(CH_3)_2$ | $CH_3$ |
| A-21 | $CH(CH_3)_2$ | $CH_2CH_3$ |
| A-22 | $CH(CH_3)_2$ | $CH_2CH_2CH_3$ |
| A-23 | $CH_2C(CH_3)_3$ | H |

TABLE A-continued

| No. | R³ | R⁴ |
|---|---|---|
| A-24 | CH₂C(CH₃)₃ | CH₃ |
| A-25 | CH₂C(CH₃)₃ | CH₂CH₃ |
| A-26 | CH₂CH(CH₃)₂ | H |
| A-27 | CH₂CH(CH₃)₂ | CH₃ |
| A-28 | CH₂CH(CH₃)₂ | CH₂CH₃ |
| A-29 | (±) CH(CH₂CH₃)CH₃ | H |
| A-30 | (±) CH(CH₂CH₃)CH₃ | CH₃ |
| A-31 | (±) CH(CH₂CH₃)CH₃ | CH₂CH₃ |
| A-32 | (R) CH(CH₂CH₃)CH₃ | H |
| A-33 | (R) CH(CH₂CH₃)CH₃ | CH₃ |
| A-34 | (R) CH(CH₂CH₃)CH₃ | CH₂CH₃ |
| A-35 | (S) CH(CH₂CH₃)CH₃ | H |
| A-36 | (S) CH(CH₂CH₃)CH₃ | CH₃ |
| A-37 | (S) CH(CH₂CH₃)CH₃ | CH₂CH₃ |
| A-38 | (±) CH(CH₃)—CH(CH₃)₂ | H |
| A-39 | (±) CH(CH₃)—CH(CH₃)₂ | CH₃ |
| A-40 | (±) CH(CH₃)—CH(CH₃)₂ | CH₂CH₃ |
| A-A1 | (R) CH(CH₃)—CH(CH₃)₂ | H |
| A-42 | (R) CH(CH₃)—CH(CH₃)₂ | CH₃ |
| A-43 | (R) CH(CH₃)—CH(CH₃)₂ | CH₂CH₃ |
| A-44 | (S) CH(CH₃)—CH(CH₃)₂ | H |
| A-45 | (S) CH(CH₃)—CH(CH₃)₂ | CH₃ |
| A-46 | (S) CH(CH₃)—CH(CH₃)₂ | CH₂CH₃ |
| A-47 | (±) CH(CH₃)—C(CH₃)₃ | H |
| A-48 | (±) CH(CH₃)—C(CH₃)₃ | CH₃ |
| A-49 | (±) CH(CH₃)—C(CH₃)₃ | CH₂CH₃ |
| A-50 | (R) CH(CH₃)—C(CH₃)₃ | H |
| A-51 | (R) CH(CH₃)—C(CH₃)₃ | CH₃ |
| A-52 | (R) CH(CH₃)—C(CH₃)₃ | CH₂CH₃ |
| A-53 | (S) CH(CH₃)—C(CH₃)₃ | H |
| A-54 | (S) CH(CH₃)—C(CH₃)₃ | CH₃ |
| A-55 | (S) CH(CH₃)—C(CH₃)₃ | CH₂CH₃ |
| A-56 | (±) CH(CH₃)—CF₃ | H |
| A-57 | (±) CH(CH₃)—CF₃ | CH₃ |
| A-58 | (±) CH(CH₃)—CF₃ | CH₂CH₃ |
| A-59 | (R) CH(CH₃)—CF₃ | H |
| A-60 | (R) CH(CH₃)—CF₃ | CH₃ |
| A-61 | (R) CH(CH₃)—CF₃ | CH₂CH₃ |
| A-62 | (H) CH(CH₃)—CF₃ | H |
| A-63 | (S) CH(CH₃)—CF₃ | CH₃ |
| A-64 | (S) CH(CH₃)—CF₃ | CH₂CH₃ |
| A-65 | (±) CH(CH₃)—CCl₃ | H |
| A-66 | (±) CH(CH₃)—CCl₃ | CH₃ |
| A-67 | (±) CH(CH₃)—CCl₃ | CH₂CH₃ |
| A-68 | (R) CH(CH₃)—CCl₃ | H |
| A-69 | (R) CH(CH₃)—CCl₃ | CH₃ |
| A-70 | (R) CH(CH₃)—CCl₃ | CH₂CH₃ |
| A-71 | (S) CH(CH₃)—CCl₃ | H |
| A-72 | (S) CH(CH₃)—CCl₃ | CH₃ |
| A-73 | (S) CH(CH₃)—CCl₃ | CH₂CH₃ |
| A-74 | CH₂C(CH₃)=CH₂ | H |
| A-75 | CH₂C(CH₃)=CH₂ | CH₃ |
| A-76 | CH₂C(CH₃)=CH₂ | CH₂CH₃ |
| A-77 | Cyclopentyl | H |
| A-78 | Cyclopentyl | CH₃ |
| A-79 | Cyclopentyl | CH₂CH₃ |
| A-80 | —(CH₂)₄— | |
| A-81 | (±) —(CH₂)₂—CH(CH₃)—CH₂— | |
| A-82 | (R) —(CH₂)₂—CH(CH₃)—CH₂— | |
| A-83 | (S) —(CH₂)₂—CH(CH₃)—CH₂— | |
| A-84 | —(CH₂)₂—CH(OCH₃)—CH₂— | |
| A-85 | —(CH₂)₂—CH(CH₂CH₃)—CH₂— | |
| A-86 | —(CH₂)₂—CH[CH(CH₃)₂]—CH₂— | |
| A-87 | —CH₂—CH=CH—CH₂— | |
| A-88 | —(CH₂)₅— | |
| A-89 | —(CH₂)₂—CH(CH₃)—(CH₂)₂— | |
| A-90 | (±) —(CH₂)₃—CH(CH₃)—CH₂— | |
| A-91 | (R) —(CH₂)₃—CH(CH₃)—CH₂— | |
| A-92 | (S) —(CH₂)₃—CH(CH₃)—CH₂— | |
| A-93 | —(CH₂)₂—C(O[CH₂]₂O)—(CH₂)₂— | |
| A-94 | —(CH₂)₂—C(O[CH₂]₃O)—(CH₂)₂— | |
| A-95 | —(CH₂)₂—C(CH₂)(CH₂)—CH₂— (cyclopropyl group) | |
| A-96 | —(CH₂)₂—CH=CH—CH₂— | |
| A-97 | —(CH₂)₂—O—(CH₂)₂— | |
| A-98 | —CH₂—CH(CH₃)—O—CH(CH₃)—CH₂— | |
| A-99 | (cis) —CH₂—CH(CH₃)—O—CH(CH₃)—CH₂— | |
| A-100 | (trans) —CH₂—CH(CH₃)—O—CH(CH₃)—CH₂— | |
| A-101 | —(CH₂)₂—NH—(CH₂)₂— | |
| A-102 | —(CH₂)₂—N(CH₃)—(CH₂)₂ | |
| A-103 | —(CH₂)₂—S—(CH₂)₂— | |
| A-104 | —(CH₂)₂—CHF—(CH₂)₂— | |
| A-105 | —(CH₂)₃—CHF—CH₂— | |
| A-106 | —(CH₂)₂—CH(CF₃)—(CH₂)₂— | |
| A-107 | —(CH₂)₂—CH(CH₂F)—(CH₂)₂— | |
| A-108 | —(CH₂)₂—CF₂—(CH₂)₂— | |

The compounds I are suitable as fungicides. They are distinguished by an outstanding activity against a broad spectrum of phytopathogenic fungi, in particular from the classes of the Ascomycetes, Deuteromycetes, Phycomycetes and Basidiomycetes. Some of them act systemically, and they can be employed in crop protection as foliar- and soil-acting fungicides.

They are especially important for controlling a large number of fungi on a variety of crop plants such as wheat, rye, barley, oats, rice, maize, grass, bananas, cotton, soya, coffee, sugar cane, grapevines, fruit species, ornamentals and vegetables such as cucumbers, beans, tomatoes, potatoes and cucurbits, and on the seeds of these plants.

Specifically, they are suitable for controlling the following plant diseases:

*Alternaria* species on vegetables and fruit,
*Botrytis cinerea* (gray mold) on strawberries, vegetables, ornamentals and grapevines,
*Cercospora arachidicola* on peanuts,
*Erysiphe cichoracearum* and *Sphaerotheca fuliginea* on cucurbits,
*Erysiphe graminis* (powdery mildew) on cereals,
*Fusarium* and *Verticillium* species on various plants,
*Helminthosporium* species on cereals,
*Mycosphaerella* species on bananas and peanuts,
*Phytophthora infestans* on potatoes and tomatoes,
*Plasmopara viticola* on grapevines,
*Podosphaera leucotricha* on apples,
*Pseudocercosporella herpotrichoides* on wheat and barley,
*Pseudocercosporella* species on hops and cucumbers,
*Puccinia* species on cereals,
*Pyricularia oryzae* on rice,
*Rhizoctonia* species on cotton, rice and turf,
*Septoria nodorum* on wheat,
*Uncinula necator* on grapevines,
*Ustilago* species on cereals and sugar cane, and
*Venturia* species (scab) on apples and pears.

Moreover, the compounds I are suitable for controlling harmful fungi such as *Paecilomyces variotii* in the protection of materials (eg. timber, paper, paint dispersions, fibers and fabrics) and in the protection of stored products.

The compounds I are applied by treating the fungi, or the plants, seeds, materials or the soil to be protected against fungal infection with a fungicidally active amount of the active ingredients. Application can be effected either before or after infection of the materials, plants or seeds by the fungi.

In general, the fungicidal compositions comprise between 0.1 and 95, preferably between 0.5 and 90, % by weight of the active ingredient.

When used in crop protection, the application rates are from 0.01 to 2.0 kg of active ingredient per hectare, depending on the nature of the desired effect.

In the treatment of seed, amounts of active ingredient of from 0.001 to 0.1 g, preferably 0.01 to 0.05 g, are generally required per kilogram of seed.

When used in the protection of materials or stored products, the rate of application of active ingredient depends on the nature of the field of application and on the desired effect. Rates of application conventionally used in the protection of materials are, for example, from 0.001 g to 2 kg, preferably 0.005 g to 1 kg, of active ingredient per cubic meter of material treated.

The compounds I can be converted into the customary formulations, eg. solutions, emulsions, suspensions, dusts, powders, pastes and granules. The use form depends on the intended purpose; it is intended to ensure in each case a fine and uniform distribution of the compound according to the invention.

The formulations are prepared in a known manner, eg. by extending the active ingredient with solvents and/or carriers, if desired using emulsifiers and dispersants, it also being possible to use other organic solvents as auxiliary solvents if water is used as the diluent. Auxiliaries which are suitable are essentially: solvents such as aromatics (eg. xylene), chlorinated aromatics (eg. chlorobenzenes), paraffins (eg. mineral oil fractions), alcohols (eg. methanol, butanol), ketones (eg. cyclohexanone), amines (eg. ethanolamine, dimethylformamide) and water; carriers such as ground natural minerals (eg. kaolins, clays, talc, chalk) and ground synthetic minerals (eg. highly disperse silica, silicates); emulsifiers such as nonionic and anionic emulsifiers (eg. polyoxyethylene fatty alcohol ethers, alkylsulfonates and arylsulfonates) and dispersants such as lignin-sulfite waste liquors and methylcellulose.

Suitable surfactants are alkali metal, alkaline earth metal and ammonium salts of lignosulfonic acid, naphthalenesulfonic acid, phenolsulfonic acid, dibutylnaphthalenesulfonic acid, alkylarylsulfonates, alkyl sulfates, alkylsulfonates, fatty alcohol sulfates and fatty acids and their alkali metal and alkaline earth metal salts, salts of sulfated fatty alcohol glycol ether, condensates of sulfonated naphthalene and naphthalene derivatives with formaldehyde, condensates of naphthalene or of napthalenesulfonic acid with phenol or formaldehyde, polyoxyethylene octylphenyl ether, ethoxylated isooctylphenol, octylphenol, nonylphenol, alkylphenyl polyglycol ethers, tributylphenyl polyglycol ether, alkylaryl polyether alcohols, isotridecyl alcohol, fatty alcohol/ethylene oxide condensates, ethoxylated castor oil, polyoxyethylene alkyl ethers, ethoxylated polyoxypropylene, lauryl alcohol polyglycol ether acetal, sorbitol esters, lignin-sulfite waste liquors and methylcellulose.

Substances which are suitable for the preparation of directly sprayable solutions, emulsions, pastes or oil dispersions are mineral oil fractions of medium to high boiling point, such as kerosene or diesel oil, furthermore coal tar oils and oils of vegetable or animal origin, aliphatic, cyclic and aromatic hydrocarbons, eg. benzene, toluene, xylene, paraffin, tetrahydronaphthalene, alkylated naphthalenes or their derivatives, methanol, ethanol, propanol, butanol, chloroform, carbon tetrachloride, cyclohexanol, cyclohexanone, chlorobenzene, isophorone, strongly polar solvents, eg. dimethylformamide, dimethyl sulfoxide, N-methylpyrrolidone and water.

Powders, materials for spreading and dusts can be prepared by mixing or concomitantly grinding the active substances with a solid carrier.

Granules, eg. coated granules, impregnated granules and homogeneous granules, can be prepared by binding the active ingredients to solid carriers. Examples of solid carriers are mineral earths, such as silicas, silica gels, silicates, talc, kaolin, attaclay, limestone, lime, chalk, bole, loess, clay, dolomite, diatomaceous earth, calcium sulfate, magnesium sulfate, magnesium oxide, ground synthetic materials, fertilizers, eg. ammonium sulfate, ammonium phosphate, ammonium nitrate, ureas, and products of vegetable origin, such as cereal meal, tree bark meal, wood meal and nutshell meal, cellulose powders and other solid carriers.

In general, the formulations comprise from 0.01 to 95% by weight, preferably from 0.1 to 90% by weight, of the active ingredient. The active ingredients are employed in a purity of from 90% to 100%, preferably 95% to 100% (according to NMR spectrum).

The following are examples of formulations:

I. 5 parts by weight of a compound according to the invention are mixed intimately with 95 parts by weight of finely divided kaolin. This gives a dust which comprises 5% by weight of the active ingredient.

II. 30 parts by weight of a compound according to the invention are mixed intimately with a mixture of 92 parts by weight of pulverulent silica gel and 8 parts by weight of paraffin oil which had been sprayed onto the surface of this silica gel. This gives a formulation of the active ingredient with good adhesion properties (comprises 23% by weight of active ingredient).

III. 10 parts by weight of a compound according to the invention are dissolved in a mixture composed of 90 parts by weight of xylene, 6 parts by weight of the adduct of 8 to 10 mol of ethylene oxide and 1 mol of oleic acid N-monoethanolamide, 2 parts by weight of calcium dodecylbenzenesulfonate and 2 parts by weight of the adduct of 40 mol of ethylene oxide and 1 mol of castor oil (comprises 9% by weight of active ingredient).

IV. 20 parts by weight of a compound according to the invention are dissolved in a mixture composed of 60 parts by weight of cyclohexanone, 30 parts by weight of isobutanol, 5 parts by weight of the adduct of 7 mol of ethylene oxide and 1 mol of isooctylphenol and 5 parts by weight of the adduct of 40 mol of ethylene oxide and 1 mol of castor oil (comprises 16% by weight of active ingredient).

V. 80 parts by weight of a compound according to the invention are mixed thoroughly with 3 parts by weight of sodium diisobutylnaphthalene-α-sulfonate, 10 parts by weight of the sodium salt of a lignosulfonic acid from a sulfite waste liquor and 7 parts by weight of pulverulent silica gel, and the mixture is ground in a hammer mill (comprises 80% by weight of active ingredient).

VI. 90 parts by weight of a compound according to the invention are mixed with 10 parts by weight of N-methyl-α-pyrrolidone, which gives a solution which is suitable for use in the form of microdrops (comprises 90% by weight of active ingredient).

VII. 20 parts by weight of a compound according to the invention are dissolved in a mixture composed of 40 parts by weight of cyclohexanone, 30 parts by weight of isobutanol, 20 parts by weight of the adduct of 7 mol of ethylene oxide and 1 mol of isooctylphenol and 10 parts by weight of the adduct of 40 mol of ethylene oxide and 1 mol of castor oil. Pouring the solution into 100,000 parts by weight of water and finely distributing it therein gives an aqueous dispersion which comprises 0.02% by weight of the active ingredient.

VIII. 20 parts by weight of a compound according to the invention are mixed thoroughly with 3 parts by weight of sodium diisobutylnaphthalene-α-sulfonate, 17 parts by weight of the sodium salt of a lignosulfonic acid from a sulfite waste liquor and 60 parts by weight of pulverulent silica gel, and the mixture is ground in a hammer mill. Finely distributing the mixture in 20,000 parts by weight of water gives a spray mixture which comprises 0.1% by weight of the active ingredient.

The active ingredients can be used as such, in the form of their formulations or the use forms prepared therefrom, eg. in the form of directly sprayable solutions, powders, suspensions or dispersions, emulsions, oil dispersions, pastes, dusts, materials for spreading, or granules, by means of spraying, atomizing, dusting, spreading or pouring. The use forms depend entirely on the intended purposes; it is intended to ensure in each case the finest possible distribution of the active ingredients according to the invention.

Aqueous use forms can be prepared from emulsion concentrates, pastes or wettable powders (sprayable powders, oil dispersions) by adding water. To prepare emulsions, pastes or oil dispersions, the substances, as such or dissolved in an oil or solvent, can be homogenized in water by means of wetter, tackifier, dispersant or emulsifier. Alternatively, it is possible to prepare concentrates composed of active substance, wetter, tackifier, dispersant or emulsifier and, if appropriate, solvent or oil, and such concentrates are suitable for dilution with water.

The active ingredient concentrations in the ready-to-use products can be varied within relatively wide ranges. In general, they are from 0.0001 to 10%, preferably from 0.01 to 1%.

The active ingredients may also be used successfully in the ultra-low-volume process (ULV), it being possible to apply formulations comprising over 95% by weight of active ingredient, or even to apply the active ingredient without additives.

Various types of oils, herbicides, fungicides, other pesticides, or bactericides may be added to the active ingredients, if appropriate just immediately prior to use (tank mix). These agents can be admixed with the agents according to the invention in a weight ratio of 1:10 to 10:1.

In the use form as fungicides, the compositions according to the invention can also be present together with other active ingredients, eg. with herbicides, insecticides, growth regulators, fungicides or else with fertilizers. Mixing the compounds I or the compositions comprising them in the use form as fungicides with other fungicides frequently results in a broader fungicidal spectrum of action.

The following list of fungicides together with which the compounds according to the invention can be used is intended to illustrate the possible combinations, but not to impose any limitation:

- sulfur, dithiocarbamates and their derivatives, such as iron (III) dimethyldithiocarbamate, zinc dimethyldithiocarbamate, zinc ethylenebisdithiocarbamate, manganese ethylenebisdithiocarbamate, manganese zinc ethylenediaminebisdithiocarbamate, tetramethylthiuram disulfide, ammonia complex of zinc (N,N-ethylenebisdithiocarbamate), ammonia complex of zinc (N,N'-propylenebisdithiocarbamate), zinc (N,N'-propylenebisdithiocarbamate), N,N'-polypropylenebis(thiocarbamoyl)disulfide;
- nitro derivatives, such as dinitro(1-methylheptyl)phenyl crotonate, 2-sec-butyl-4,6-dinitrophenyl 3,3-dimethylacrylate, 2-sec-butyl-4,6-dinitrophenylisopropyl carbonate, diisopropyl 5-nitro-isophthalate;
- heterocyclic substances, such as 2-heptadecyl-2-imidazoline acetate, 2,4-dichloro-6-(o-chloroanilino)-s-triazine, O,O-diethyl phthalimidophosphonothioate, 5-amino-1-[bis(dimethylamino)phosphinyl]-3-phenyl-1,2,4-triazole, 2,3-dicyano-1,4-dithioanthraquinone, 2-thio-1,3-dithiolo[4,5-b]-quinoxaline, methyl 1-(butylcarbamoyl)-2-benzimidazolecarbamate, 2-methoxycarbonylaminobenzimidazole, 2-(2-furyl)-benzimidazole, 2-(4-thiazolyl)benzimidazole, N-(1,1,2,2-tetrachloroethylthio)tetrahydrophthalimide, N-trichloromethylthiotetrahydrophthalimide, N-trichloromethylthiophthalimide;
- N-dichlorofluoromethylthio-N',N'-dimethyl-N-phenylsulfodiamide, 5-ethoxy-3-trichloromethyl-1,2,3-thiadiazole, 2-thiocyanatomethylthiobenzothiazole, 1,4-dichloro-2,5-dimethoxybenzene, 4-(2-chlorophenylhydrazono)-3-methyl-5-isoxazolone, pyridine-2-thiol 1-oxide, 8-hydroxyquinoline or its copper salt, 2,3-dihydro-5-carboxanilido-6-methyl-1,4-oxathiine, 2,3-dihydro-5-carboxanilido-6-methyl-1,4-oxathiine 4,4-dioxide, 2-methyl-5,6-dihydro-4H-pyran-3-carboxanilide, 2-methylfuran-3-carboxanilide, 2,5-dimethylfuran-3-carboxanilide, 2,4,5-trimethylfuran-3-carboxanilide, 2,5-dimethylfuran-3-carbocyclohexylamide, N-cyclohexyl-N-methoxy-2,5-dimethylfuran-3-carboxamide, 2-methylbenzanilide, 2-iodobenzanilide, N-formyl-N-morpholine-2,2,2-trichloroethyl acetal, piperazine-1,4-diylbis-1-(2,2,2-trichloroethyl)formamide, 1-(3,4-dichloroanilino)-1-formylamino-2,2,2-trichloroethane, 2,6-dimethyl-N-tridecylmorpholine or its salts, 2,6-dimethyl-N-cyclododecylmorpholine or its salts, N-[3-(p-tert-butylphenyl)-2-methylpropyl]-cis-2,6-dimethylmorpholine, N-[3-(p-tert-butylphenyl)-2-methylpropyl]piperidine, 1-[2-(2,4-dichlorophenyl)-4-ethyl-1,3-dioxolan-2-yl-ethyl]-1H-1,2,4-triazole, 1-[2-(2,4-dichlorophenyl)-4-n-propyl-1,3-dioxolan-2-yl-ethyl]-1H-1,2,4-triazole, N-(n-propyl)-N-(2,4,6-trichlorophenoxyethyl)-N'-imidazolylurea, 1-(4-chlorophenoxy)-3,3-dimethyl-1-(1H-1,2,4-triazol-1-yl)-2-butanone, 1-(4-chlorophenoxy)-3,3-dimethyl-1-(1H-1,2,4-triazol-1-yl)-2-butanole, (2RS,3RS)-1-[3-(2-chlorophenyl)-2-(4-fluorophenyl)-oxiran-2-ylmethyl]-1H-1,2,4-triazole, α-(2-chlorophenyl)-α-(4-chlorophenyl)-5-pyrimidinemethanol, 5-butyl-2-dimethylamino-4-hydroxy-6-methylpyrimidine, bis(p-chlorophenyl)-3-pyridinemethanol, 1,2-bis(3-ethoxycarbonyl-2-thioureido)benzene, 1,2-bis(3-methoxycarbonyl-2-thioureido)benzene;
- strobilurins such as methyl E-methoxyimino-[α-(o-tolyloxy)-o-tolyl]acetate, methyl-E-2-{2-[6-(2-cyanophenoxy)pyrimidin-4-yloxy]-phenyl}-3-methoxyacrylate, N-methyl-E-methoxy-imino-[α-(2-phenoxyphenyl)]acetamide, N-methyl E-methoxyimino-[α-(2,5-dimethylphenoxy)-o-tolyl]acetamide, methyl E-2-{2-[2-trifluoromethylpyridyl-6-]oxymethyl]phenyl}-3-methoxyacrylate, methyl (E,E)-methoximino-{2-[1-(3-trifluoromethylphenyl)ethylidene-aminooxymethyl]phenyl}acetate, methyl-N-(2-{[1-(4-chlorophenyl)-1H-pyrazol-3-yl]oxymethyl}phenyl)N-methoxycarbamate;
- anilinopyrimidines such as N-(4,6-dimethylpyrimidin-2-yl)aniline, N-[4-methyl-6-(1-propynyl)pyrimidin-2-yl]aniline, N-[4-methyl-6-cyclopropylpyrimidin-2-yl]aniline;
- phenylpyrroles such as 4-(2,2-difluoro-1,3-benzodioxol-4-yl)pyrrole-3-carbonitrile;
- cinnamamides such as 3-(4-chlorophenyl)-3-(3,4-dimethoxy-phenyl)acryloylmorpholine;
- and a variety of fungicides such as dodecylguanidine acetate, 3-[3-(3,5-dimethyl-2-oxycyclohexyl)-2-hydroxyethyl]glutarimide, hexachlorobenzene, methyl N-(2,6-dimethylphenyl)-N-(2-furoyl)-DL-alaninate, DL-N-(2,6-dimethylphenyl)-N-(2'-methoxyacetyl)-alanine methyl ester, N-(2,6-dimethylphenyl)-N-chloroacetyl-D,L-2-amino-butyrolactone, DL-N-(2,6-dimethylphenyl)-N-(phenylacetyl)-alanine methyl ester, 5-methyl-5-vinyl-3-(3,5-dichlorophenyl)-2,4-dioxo-1,3-oxazolidine, 3-[3,5-dichlorophenyl(5-methyl-5-methoxymethyl]-1,3-oxazolidine-2,4-dione, 3-(3,5-dichlorophenyl)-1-isopropylcarbamoylhydantoin, N-(3,5-dichlorophenyl)-1,2-dimethylcyclopropane-1,2-dicarboximide, 2-cyano-[N-(ethylaminocarbonyl)-2-methoximino]acetamide, 1-[2-(2,4-dichlorophenyl) pentyl]-1H-1,2,4-triazole, 2,4-difluoro-α-(1H-1,2,4-triazolyl-1-methyl)benzhydryl alcohol, N-(3-chloro-2,6-dinitro-4-trifluoromethylphenyl)-5-trifluoromethyl-3-chloro-2-aminopyridine, 1-((bis(4-fluorophenyl)methylsilyl)methyl-1H-1,2,4-triazole.

SYNTHESIS EXAMPLES

With due modification of the starting compounds, the protocols shown in the synthesis examples below were used for obtaining further compounds I. The compounds obtained in this way are listed in the following tables with physical data.

Example 1

6-Chloro-5-(2-chloro-6-fluorophenyl)-4-isopropylamino-2-(1-pyrazolyl)pyrimidine [I-1]

a) 5-(2-Chloro-6-fluorophenyl)-2-methylthio-4,6(1H,5H)-pyrimidinedione 60.0 g (208 mmol) of ethyl 2-(2-chloro-6-fluorophenyl) malonate and 19.0 g (249 mmol) of thiourea were heated for 2.5 hours at 150° C. in 77 g (416 mmol) of n-tributylamine. Most of the ethanol formed was distilled off. 180 ml of an aqueous solution of 24.9 g (623 mmol) of NaOH were added to the reaction mixture once it had cooled down. After the aqueous phase had been treated with 50 ml of cyclohexane and stirred for approximately 30 minutes, it was separated off, treated with 35.4 g (142 mmol) of methyl iodide and stirred for approximately 16 hours at approximately 20 to 25° C. After acidification with dilute HCl solution and stirring for approximately 30 minutes, the precipitate was filtered off. Washing with water and drying gave 16.7 g of the title compound as white crystals of m.p. 250° C. (decomp.).

b) 4,6-Dichloro-5-(2-chloro-6-fluorophenyl)-2-methylthiopyrimidine

A solution of 48.8 g (170 mmol) of the product of step a in 200 ml of phosphorus oxychloride was refluxed for 40 hours after addition of 3 ml of dimethylformamide (DMF). After most of the phosphorus oxychloride had been distilled off and the residue had been diluted with ethyl acetate, water was added with stirring at 15 to 20° C. After phase separation, the organic phase was washed with water and dilute NaHCO₃ solution and then dried and freed from solvent. This gave 37.5 g of the title compound as an oil which was employed in step c without further purification. IR (film): γ[cm⁻¹]=1558, 1477, 1449, 1353, 1252, 900, 816, 783.

c) 6-Chloro-5-(2-chloro-6-fluorophenyl)-4-isopropylamino-2-methylthiopyrimidine

A solution of 37.5 g (324 mmol) of the product of step b in 150 ml of anhydrous dichloromethane was treated with 24 g (406 mol) of isopropylamine and stirred for five hours at approximately 20 to 25° C. Then, the solvent was distilled off, the residue was taken up in ethyl acetate and washed with dilute HCl, water and dilute NaHCO₃ solution, dried and freed from solvent. Following chromatography on silica gel (cyclohexane/methyl tert-butyl ether 100:1 to 19:1), 13.4 g of the title compound were obtained from the residue in the form of colorless crystals of m.p. 94-98° C., which were employed in the next step without further purification.

d) 6-Chloro-5-(2-chloro-6-fluorophenyl)-4-isopropylamino-2-methylsulfonylpyrimidine A solution of 13.3 g (38.4 mmol) of the product of step c in 240 ml of anhydrous dichloromethane was treated with 17.2 g (76.8 mmol) of 3-chloroperbenzoic acid at 0 to 5° C. The mixture was stirred for one hour at 0 to 5° C. and for 14 hours at approximately 20 to 25° C. After the solvent was distilled off, the residue was taken up in ethyl acetate and then washed with 10% strength NaHCO₃ solution. After phase separation, the organic phase was dried and freed from solvent. The residue was digested with diisopropyl ether/hexane. This gave 11.3 g of the title compound as colorless crystals of m.p. 145-149° C.

e) 6-Chloro-5-(2-chloro-6-fluorophenyl)-4-isopropylamino-2-(1-pyrazolyl)pyrimidine A solution of 180 mg (2.64 mmol) of pyrazole in 4 ml of anhydrous DMF was treated with 106 mg (2.64 mmol) of NaH (60% suspension in mineral oil), with ice-cooling. After the mixture had been stirred for one hour, 500 mg (1.32 mmol) of the product of step d were added and the mixture was stirred for approximately 14 hours at 20 to 25° C. The product was precipitated by adding water. Filtration, washing with water and drying gave 450 mg of the title compound as colorless crystals of m.p. 185-187° C.

Example 2

(S)-6-Chloro-4-(2,2,2-trifluoro-1-methylethyl)amino-5-(2,4,6-trifluorophenyl)-2-(1-pyrazolyl)pyrimidine [I-2]

a) 5-(2,4,6-Trifluorophenyl)-2-methylthio-4,6(1H,5H)-pyrimidinedione

Analogously to Example 1 (step a), 200.0 g of diethyl 2-(2,4,6-trifluorophenyl)malonate, 62.9 g of thiourea and 117.4 g of methyl iodide gave 115 g of white crystals of m.p. 275° C. (decomp.).

b) 4,6-Dichloro-5-(2,4,6-trifluorophenyl)-2-methylthiopyrimidine

The following Example 1 (step b), 64.8 g of the product of step a gave, after chromatography on silica gel with cyclohexane, 43 g of white crystals of m.p. 75° C.

c) (5)-6-Chloro-5-(2,4,6-trifluorophenyl)-4-(2,2,2-trifluoro-2-methylethylamino)-2-methylthiopyrimidine A solution of 90.0 g (277 mmol) of the product of step b and 120.0 g (113 mmol) of 2,2,2-trifluoro-1-methylethylamine was stirred for five days at 150° C. After dilution with methyl tert-butyl ether and washing with 5M hydrochloric acid, the phases were separated. The organic phase was dried and then freed from solvent. Chromatography on silica gel (cyclohexane, then cyclohexane/methyl tert-butyl ether 85:15) gave 90 g of the title compound as colorless crystals of m.p. 94-96° C.

d) (S)-6-Chloro-5-(2,4,6-trifluorophenyl)-4-(2,2,2-trifluoro-1-methylethylamino)-2-methylsulfonylpyrimidine Analogously to Example 1 (step d), 90.0 g (424 mmol) of the product of step c gave 89 g (92% of theory) of white crystals of m.p. 159° C.

e) (S)-6-Chloro-4-(2,2,2-trifluoro-1-methylethyl)amino-5-(2,4,6-trifluorophenyl)-2-(1-pyrazolyl)pyrimidine Analogously to Example 1 (step e), 17.0 g (39.2 mmol) of the product of step d and 4.00 g (58.8 mmol) of pyrazole gave 14.9 g (90% of theory) of the title compound in the form of colorless crystals of m.p. 209° C. (purity 97% according to HPLC analysis).

Example 3

(S)-6-Chloro-4-(2,2,2-trifluoro-1-methylethyl)amino-5-(2,4,6-trifluorophenyl)-2-(1-imidazolyl)pyrimidine [I-3]

Analogously to Example 1 (step e), 89.8 mg of imidazole and 249.5 g of the sulfone of Example 1, in step d, gave 0.22 g (91% of theory) of the title compound in the form of colorless crystals of m.p. 172-173° C.

Example 4

(S)-6-Chloro-4-(2,2,2-trifluoro-1-methylethyl)amino-5-(2,4,6-trifluorophenyl)-2-(1,2,4-triazol-1-yl)pyrimidine [I-4]

Analogously to Example 1 (step e), 91.1 mg of 1,2,4-triazole and 24.95 g of the sulfone of Example 1, step d, gave 0.22 g (91% of theory) of the title compound in the form of colorless crystals of m.p. 176-177° C.

Example 5

6-Chloro-5-(2,4,6-trifluorophenyl)-4-[(S)-1,2-dimethyl-propyl]-amino-2-(pyridazin-3-yl)-pyrimidine [I-5]

a) Pyridazine-3-carboxamidine

A solution of 1.60 g (0.068 mol) of sodium in 300 ml of anhydrous methanol was treated with a solution of 53.5 g (0.510 mol) of pyridazine-3-carbonitrile in 100 ml of methanol and the mixture was stirred for 8 hours at 35° C. Then, 29 g of ammonium chloride were added and the mixture was refluxed for approximately 14 hours. The hot mixture was filtered and the solid was discarded. 53.3 g of the title compound were obtained from the cold mother liquor by means of filtration.

$^1$H NMR: δ (ppm, DMSO-$d_6$)=9.75 (bs); 9.6 (d); 8.6 (d); 8.1 (m).

b) 4,6-Dihydroxy-5-(2,4,6-trifluorophenyl)-2-(3-pyridazinyl)-pyrimidine

A mixture of 18.1 g (0.063 mol) of diethyl 2-(2,4,6-trifluorophenyl)malonate, 12 g (0.063 mol) of tributylamine and 10.0 g (0.063 mol) of the amidine of Ex. 5a was heated for approximately 6 hours at 180° C., during which process ethanol distilled off. After cooling to 60-70° C., the mixture was treated with 6.3 g (0.158 mol) of sodium hydroxide, dissolved in 70 ml of water, and stirring was continued for 30 minutes. After cooling to 20-25° C., the mixture was extracted with MTBE, and the reaction product was precipitated from the aqueous phase by acidification. Filtration gave 6.0 g of the title compound.

$^1$H NMR: δ (ppm, DMSO-$d_6$)=9.5 (d); 8.2 (d); 8.0 (dd); 7.2 (m).

c) 4,6-Dichloro-5-(2,4,6-trifluorophenyl)-2-(3-pyridazinyl)-pyrimidine

A suspension of 5.7 g (0.018 mol) of the dihydroxypyrimidine of Ex. 5b in 37 g (0.23 mol) of phosphorus oxychloride was heated for 8 hours at 120° C. and then concentrated in vacuo. The residue was taken up in dichloromethane and water, and the organic phase was dried and freed from solvent. Chromatography on silica gel (cyclohexane/ethyl acetate) gave 2.0 g of the title compound.

$^1$H NMR: δ (ppm, CDCl$_3$)=9.2 (d); 8.7 (d); 7.8 (dd); 6.9 (t).

d) 6-Chloro-5-(2,4,6-trifluorophenyl)-4-[(S)-1,2-dimethyl-propyl]amino-2-(pyridazin-3-yl)-pyrimidine A solution of 200 mg (0.568 mmol) of the dichloride of Ex. 5c in 5 ml of DMF was treated with 100 mg (1.2 mmol) of (S)-3-methyl-2-butylamine and the mixture was then stirred for 72 hours at 50° C. and then cooled to 20-25° C. The reaction product was precipitated by addition of water. Filtration gave 200 mg (100% of theory) of the title compound.

$^1$H NMR: δ (ppm, CDCl$_3$)=9.3 (d); 8.5 (d); 7.6 (dd); 6.9 (t); 4.5 (m); 4.4 (m); 1.8 (m); 1.1 (d); 0.9 (d).

TABLE I

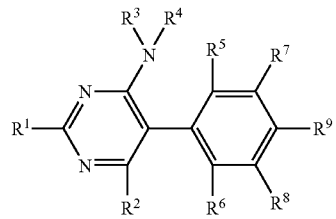

| No. | R¹ | R² | R³ | R⁴ | R⁵ | R⁶ | R⁷ | R⁸ | R⁹ | Physical data (M.p.[° C.], $^1$H NMR[ppm]; $logP_{ow}$ |
|---|---|---|---|---|---|---|---|---|---|---|
| I-1 | pyrazolyl-1 | Cl | CH(CH₃)₂ | H | Cl | F | H | H | H | 185-187 |
| I-2 | pyrazolyl-1 | Cl | (S) CH(CH₃)CF₃ | H | F | F | H | H | F | 159 |
| I-3 | imidazolyl-1 | Cl | (S) CH(CH₃)CF₃ | H | F | F | H | H | F | 203-205 |
| I-4 | 1,2,4-triazolyl-1 | Cl | (S) CH(CH₃)CF₃ | H | F | F | H | H | F | 112-114 |
| I-5 | pyridazinyl-3 | Cl | (S) CH(CH₃)CH(CH₃)₂ | H | F | F | H | H | F | 176 |
| I-6 | pyrimidinyl-2 | Cl | (R) CH(CH₃)CH(CH₃)₂ | H | Cl | F | H | H | H | 228 |
| I-7 | pyrimidinyl-2 | Cl | CH(CH₃)₂ | H | Cl | F | H | H | H | 157 |
| I-8 | pyrimidinyl-2 | Cl | c-C₅H₉ | H | Cl | F | H | H | H | 167 |
| I-9 | pyrimidinyl-2 | Cl | CH₂CH₃ | CH₂CH₃ | Cl | F | H | H | H | $logP_{ow}$ 3.86 |
| I-10 | pyrimidinyl-2 | Cl | (S) CH(CH₃)C(CH₃)₃ | H | Cl | F | H | H | H | 224-226 |
| I-11 | pyrimidinyl-2 | Cl | CH(CH₃)₂ | H | F | F | H | H | F | $logP_{ow}$ 3.15 |
| I-12 | pyrazinyl | Cl | (S) CH(CH₃)C(CH₃)₃ | H | Cl | F | H | H | H | 0.9 (d, 9H); 1.1 (dd, 3H); 4.4 (m, 2H); 7.2 (m, 1H); 7.45 (m, 2H); 8.7 (s, 1H); 8.8 (s, 1H); 9.7 (s, 1H) |
| I-13 | pyrazinyl | Cl | CH(CH₃)₂ | H | Cl | F | H | H | H | 153 |
| I-14 | pyrazinyl | Cl | CH₂CH₃ | CH₂CH₃ | Cl | F | H | H | H | $logP_{ow}$ 4.49 |
| I-15 | pyrazinyl | Cl | —(CH₂)₂—CH(CH₃)—(CH₂)₂— | | Cl | F | H | H | H | 0.9 (d, 3H); 1.1 (m, 2H); 1.6 (m, 3H); 2.9 (m, 2H); 4.1 (m, 2H); 7.1 (t, 1H); 7.4 (m, 2H); 8.7 (s, 1H); 8.8 (s, 1H); 9.65 (s, 1H) |
| I-16 | pyrazinyl | Cl | CH₂C(=CH₂)CH₃ | CH₂CH₃ | Cl | F | H | H | H | 1.1 (t, 3H); 1.45 (s, 3H); 3.3 (m, 1H); 3.6 (m, 1H); 3.9 (dd, 2H); 4.8 (m, 2H); 7.1 (t, 1H); 7.3 (m, 1H); 7.4 (m, 1H); 8.65 (d, 1H); 8.8 (s, 1H); 9.6 (s, 1H) |
| I-17 | pyrazinyl | Cl | (S) CH(CH₃)CF₃ | H | Cl | F | H | H | H | 1.15 (s, 3H); 4.7 (d, 1H); 5.3 (m, 1H); 7.2 (m, 1H); 7.5 (m, 2H); 8.7 (s, 1H); 8.8 (s, 1H); 9.6 (s, 1H) |
| I-18 | pyrazinyl | Cl | CH(CH₃)₂ | H | F | F | H | H | F | $logP_{ow}$ 4.7 |
| I-19 | pyrazinyl | Cl | CH(CH₃)CH₂CH₃ | H | F | F | H | H | F | 175-176 |
| I-20 | pyrazinyl | Cl | CH₂CH₃ | CH₂CH₃ | F | F | H | H | F | $logP_{ow}$ 4.41 |
| I-21 | pyrazinyl | Cl | CH(CH₃)₂ | CH₃ | F | F | H | H | F | $logP_{ow}$ 4.48 |
| I-22 | pyrazinyl | Cl | CH₂C(CH₃)₃ | H | F | F | H | H | F | $logP_{ow}$ 4.72 |
| I-23 | pyrazinyl | Cl | (S) CH(CH₃)CF₃ | H | F | F | H | H | F | 188 |
| I-24 | pyrazinyl | Cl | CH₂C(=CH₂)CH₃ | CH₂CH₃ | F | F | H | H | F | 1.1 (t, 3H); 1.4 (s, 3H); 3.5 (q, 2H); 3.9 (s, 2H); 4.8 (d, 2H); 6.8 (t, 2H); 8.7 (s, 1H); 8.8 (s, 1H); 9.6 (s, 1H) |
| I-25 | pyrazinyl | Cl | (S) CH(CH₃)C(CH₃)₃ | H | F | F | H | H | F | 128 |
| I-26 | pyridazinyl-3 | Cl | CH(CH₃)C(CH₃)₃ | H | F | F | H | H | F | 126 |
| I-27 | pyrazolyl-1 | Cl | H | H | F | F | H | H | F | 317-319 |
| I-28 | imidazolyl-1 | Cl | CH(CH₃)₂ | H | Cl | F | H | H | H | 172-173 |
| I-29 | 1,2,4-triazolyl-1 | Cl | CH(CH₃)₂ | H | Cl | F | H | H | H | 176-177 |
| I-30 | Tetrazolyl-1 | Cl | CH(CH₃)₂ | H | Cl | F | H | H | H | 171-175 |
| I-31 | 1,2,5-triazolyl-1 | Cl | CH(CH₃)₂ | H | Cl | F | H | H | H | 170-173 |
| I-32 | 1,2,3-triazolyl-1 | Cl | CH(CH₃)₂ | H | Cl | F | H | H | H | 153-157 |
| I-33 | 3-CF₃-pyrazolyl-1 | Cl | CH(CH₃)₂ | H | Cl | F | H | H | H | 184-186 |
| I-34 | 4-Br-pyrazolyl-1 | Cl | CH(CH₃)₂ | H | Cl | F | H | H | H | 128-132 |
| I-35 | 3-CH₃-pyrazolyl-1 | Cl | CH(CH₃)₂ | H | Cl | F | H | H | H | 174-179 |
| I-36 | pyrazolyl-1 | Cl | CH(CH₃)₂ | H | F | F | H | H | F | 206-209 |
| I-37 | 1,2,4-triazolyl-1 | Cl | CH(CH₃)₂ | H | F | F | H | H | F | 212-214 |
| I-38 | imidazolyl-1 | Cl | CH(CH₃)₂ | H | F | F | H | H | F | 215-216 |
| I-39 | 3-CF₃-pyrazolyl-1 | Cl | CH(CH₃)₂ | H | F | F | H | H | F | 234-236 |

TABLE I-continued

Structure: pyrimidine with R¹ at 2-position, R² at 6-position, NR³R⁴ at 4-position, phenyl(R⁵-R⁹) at 5-position.

| No. | R¹ | R² | R³ | R⁴ | R⁵ | R⁶ | R⁷ | R⁸ | R⁹ | Physical data (M.p.[° C.], ¹H NMR[ppm]; logP$_{ow}$) |
|---|---|---|---|---|---|---|---|---|---|---|
| I-40 | 4-Br-pyrazolyl-1 | Cl | CH(CH₃)₂ | H | F | F | H | H | F | 1.2 (d, 6H); 4.3 (m, 1H); 4.7 (m, 1H); 6.85 (m, 2H); 7.8 (s, 1H); 8.4 (s, 1H) |
| I-41 | 3-CH₃-pyrazolyl-1 | Cl | CH(CH₃)₂ | H | F | F | H | H | F | 1.2 (d, 6H); 4.3 (m, 2H); 6.2 (d, 1H); 6.8 (m, 2H); 8.4 (d, 1H) |
| I-42 | 3,5-(CH₃)₂, 4-Cl-pyrazolyl-1 | Cl | CH(CH₃)₂ | H | F | F | H | H | F | 241–244 |
| I-43 | 3,5-(CH₃)₂-pyrazolyl-1 | Cl | CH(CH₃)₂ | H | F | F | H | H | F | 206–211 |
| I-44 | 5-NO₂-indazol-1-yl | Cl | CH(CH₃)₂ | H | F | F | H | H | F | 179–184 |
| I-45 | 3-[CH(CH₃)₂]-pyrazolyl-1 | Cl | CH(CH₃)₂ | H | F | F | H | H | F | 229–235 |
| I-46 | 5-NO₂-pyrazolyl-1 | Cl | CH(CH₃)₂ | H | F | F | H | H | F | 188–194 |
| I-47 | 4-CH₃-pyrazolyl-1 | Cl | CH(CH₃)₂ | H | F | F | H | H | F | 172–174 |
| I-48 | 4-(4-CH₃—C₆H₄)-pyrazolyl-1 | Cl | CH(CH₃)₂ | H | F | F | H | H | F | 197–201 |
| I-49 | 1H-Indazolyl-1 | Cl | CH(CH₃)₂ | H | F | F | H | H | F | 192–194 |
| I-50 | 3-C₆H₅-pyrazolyl-1 | Cl | CH(CH₃)₂ | H | F | F | H | H | F | 196–198 |
| I-51 | 1,2,3-triazolyl-1 | Cl | (S) CH(CH₃)CF₃ | H | F | F | H | H | F | 160–163 |
| I-52 | 1,2,5-triazolyl-1 | Cl | (S) CH(CH₃)CF₃ | H | F | F | H | H | F | 172–173 |
| I-53 | 4-CH₃-pyrazolyl-1 | Cl | (S) CH(CH₃)CF₃ | H | F | F | H | H | F | 214–218 |
| I-54 | 4-Br-pyrazolyl-1 | Cl | (S) CH(CH₃)CF₃ | H | F | F | H | H | F | 160–163 |
| I-55 | 3,5-(CH₃)₂, 4-Cl-pyrazolyl-1 | Cl | (S) CH(CH₃)CF₃ | H | F | F | H | H | F | 235–238 |
| I-56 | 3-C₆H₅-pyrazolyl-1 | Cl | (S) CH(CH₃)CF₃ | H | F | F | H | H | F | 185–190 |
| I-57 | 5-NO₂-indazol-1-yl | Cl | (S) CH(CH₃)CF₃ | H | F | F | H | H | F | 165–168 |
| I-58 | 3-[CH(CH₃)₂]-pyrazolyl-1 | Cl | (S) CH(CH₃)CF₃ | H | F | F | H | H | F | 270–273 |
| I-59 | 3-CF₃-pyrazolyl-1 | Cl | (S) CH(CH₃)CF₃ | H | F | F | H | H | F | 253–255 |
| I-60 | 5-NO₂-pyrazolyl-1 | Cl | (S) CH(CH₃)CF₃ | H | F | F | H | H | F | 222–224 |
| I-61 | 3-(3-CH₃-C₆H₄)-4-(CO₂CH₃)-5-CH₃-pyrazolyl-1 | Cl | (S) CH(CH₃)CF₃ | H | F | F | H | H | F | 1.3 (d, 3H); 2.3 (s, 3H); 3.0 (s, 3H); 3.8 (s, 3H); 4.8 (bm, 1H); 5.2 (bm, 1H); 6.9 (m, 2H); 7.1–7.4 (bm, 4H) |
| I-62 | 4-(4-CH₃—C₆H₄)-pyrazolyl-1 | Cl | (S) CH(CH₃)CF₃ | H | F | F | H | H | F | 214–216 |
| I-63 | 3,5(CH₃)₂, 4-I-pyrazolyl-1 | Cl | (S) CH(CH₃)CF₃ | H | F | F | H | H | F | 228–232 |
| I-64 | 3-CH₃, 4-Br-pyrazolyl-1 | Cl | (S) CH(CH₃)CF₃ | H | F | F | H | H | F | 242–244 |
| I-65 | 4-I-pyrazolyl-1 | Cl | (S) CH(CH₃)CF₃ | H | F | F | H | H | F | 194–196 |

TABLE I-continued

Structure: pyrimidine with R¹ at 2-position, R² at 6-position (bottom), NR³R⁴ at 4-position, and a phenyl ring at 5-position bearing R⁵, R⁶, R⁷, R⁸, R⁹.

| No. | R¹ | R² | R³ | R⁴ | R⁵ | R⁶ | R⁷ | R⁸ | R⁹ | Physical data (M.p.[° C.], ¹H NMR[ppm]; logP$_{ow}$) |
|---|---|---|---|---|---|---|---|---|---|---|
| I-66 | 3-CF₃, 4-(H₃COOC)-pyrazolyl-1 | Cl | (S) CH(CH₃)CF₃ | H | F | F | H | H | F | 214-6 |
| I-67 | Br₃-pyrazolyl-1 | Cl | (S) CH(CH₃)CF₃ | H | F | F | H | H | F | 206-209 |
| I-68 | 3,5-(CH₃)₂, 4-Br-pyrazolyl-1 | Cl | (S) CH(CH₃)CF₃ | H | F | F | H | H | F | 258-261 |
| I-69 | 4-Cl-pyrazolyl-1 | Cl | (S) CH(CH₃)CF₃ | H | F | F | H | H | F | 185-188 |
| I-70 | 3-CH₃, 5-(COOCH₂CH₃)-pyrazolyl-1 | Cl | (S) CH(CH₃)CF₃ | H | F | F | H | H | F | 180-182 |
| I-71 | 3-CH₃, 4-Cl-pyrazolyl-1 | Cl | (S) CH(CH₃)CF₃ | H | F | F | H | H | F | 247-249 |
| I-72 | 3-NO₂-1,2,4-triazolyl-1 | Cl | (S) CH(CH₃)CF₃ | H | F | F | H | H | F | 131-135 |
| I-73 | 3-NO₂, 5-Br-1,2,4-triazolyl-1 | Cl | (S) CH(CH₃)CF₃ | H | F | F | H | H | F | >350 |
| I-74 | 6-Cl-1H-benzotriazolyl-1 | Cl | (S) CH(CH₃)CF₃ | H | F | F | H | H | F | 140-142 |
| I-75 | 1H-benzotriazolyl-1 | Cl | (S) CH(CH₃)CF₃ | H | F | F | H | H | F | 100-102 |
| I-76 | 6-CH₃-1H-benzotriazolyl-1 | Cl | (S) CH(CH₃)CF₃ | H | F | F | H | H | F | 118-121 |
| I-77 | 6-NO₂-1H-benzotriazolyl-1 | Cl | (S) CH(CH₃)CF₃ | H | F | F | H | H | F | 130-133 |
| I-78 | imidazo[4,5-b]pyridin-1-yl | Cl | (S) CH(CH₃)CF₃ | H | F | F | H | H | F | 140-143 |
| I-79 | 1H-benzoimidazolyl-1 | Cl | (S) CH(CH₃)CF₃ | H | F | F | H | H | F | 127-130 |
| I-80 | 2-CH₃, 4-NO₂-imidazolyl-1 | Cl | (8) CH(CH₃)CF₃ | H | F | F | H | H | F | 132-135 |
| I-81 | 1-methylxanthin-7-yl | Cl | (S) CH(CH₃)CF₃ | H | F | F | H | H | F | 125-127 |
| I-82 | imidazolyl-1 | Cl | —(CH₂)₂—CH(CH₃)—(CH₂)₂— | | F | F | H | H | F | 0.9 (d, 3H); 1.1 (m, 2H); 2.5 (m, 3H); 2.9 (m, 2H); 4.0 (m, 2H); 6.8 (m, 2H); 7.9 (s, 1H); 8.4 (s, 1H) |
| I-83 | 1,2,4-triazolyl-1 | Cl | —(CH₂)₂—CH(CH₃)—(CH₂)₂— | | F | F | H | H | F | 95–98 |
| I-84 | 1,2,3-triazolyl-1 | Cl | —(CH₂)₂—CH(CH₃)—(CH₂)₂— | | F | F | H | H | F | 124–128 |
| I-85 | 3,5-(CH₃)₂, 4-Cl-pyrazolyl-1 | Cl | —(CH₂)₂—CH(CH₃)—(CH₂)₂— | | F | F | H | H | F | 146-148 |
| I-86 | 3,5-(CH₃)₂-pyrazolyl-1 | Cl | —(CH₂)₂—CH(CH₃)—(CH₂)₂ | | F | F | H | H | F | 127-131 |

TABLE I-continued

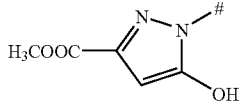

| No. | R¹ | R² | R³ R⁴ | R⁵ | R⁶ | R⁷ | R⁸ | R⁹ | Physical data (M.p.[° C.], $^1$H NMR[ppm]; $logP_{ow}$) |
|---|---|---|---|---|---|---|---|---|---|
| I-87 | 3-C₆H₅-pyrazolyl-1 | Cl | —(CH₂)₂—CH(CH₃)—(CH₂)₂— | F | F | H | H | F | 179-181 |
| I-88 | 3-CF₃-pyrazolyl-1 | Cl | —(CH₂)₂—CH(CH₃)—(CH₂)₂— | F | F | H | H | F | 101-102 |
| I-89 | 5-NO₂-pyrazolyl-1 | Cl | —(CH₂)₂—CH(CH₃)—(CH₂)₂— | F | F | H | H | F | 158-161 |
| I-90 | H₃COOC-pyrazolyl (with OH) | Cl | —(CH₂)₂—CH(CH₃)—(CH₂)₂— | F | F | H | H | F | 110-112 |
| I-91 | 1H-indazolyl-1 | Cl | —(CH₂)₂—CH(CH₃)—(CH₂)₂— | F | F | H | H | F | 145-150 |
| I-92 | 3,5-(CH₃)₂, 4-I-pyrazolyl-1 | Cl | —(CH₂)₂—CH(CH₃)—(CH₂)₂— | F | F | H | H | F | 158-161 |
| I-93 | 3-CH₃, 4-Br-pyrazolyl-1 | Cl | —(CH₂)₂—CH(CH₃)—(CH₂)₂— | F | F | H | H | F | 136-138 |
| I-94 | Br₃-pyrazolyl-1 | Cl | —(CH₂)₂—CH(CH₃)—(CH₂)₂— | F | F | H | H | F | 121-125 |
| I-95 | 4-I-pyrazolyl-1 | Cl | —(CH₂)₂—CH(CH₃)—(CH₂)₂— | F | F | H | H | F | 174-177 |
| I-96 | 3-CH₃-pyrazolyl-1 | Cl | —(CH₂)₂—CH(CH₃)—(CH₂)₂— | F | F | H | H | F | 0.9 (d, 3H); 1.1 (m, 2H); 1.4 (m, 3H); 2.4 (s, 3H); 2.8 (m, 2H); 4.1 (m, 2H); 6.2 (d, 1H); 6.8 (m, 2H); 8.3 (d, 1H) |
| I-97 | 4-Br-pyrazolyl-1 | Cl | —(CH₂)₂—CH(CH₃)—(CH₂)₂— | F | F | H | H | F | 131-134 |
| I-98 | 3-[CH(CH₃)₂]-pyrazolyl-1 | Cl | —(CH₂)₂—CH(CH₃)—(CH₂)₂— | F | F | H | H | F | 0.9 (d, 3H); 1.1 (m, 2H); 1.2 (d, 6H); 1.4 (m, 3H); 2.9 (m, 2H); 4.0 (m, 2H); 6.2 (s, 1H); 6.8 (m, 2H); 8.4 (s, 1H) |
| I-99 | 3,5-(CH₃)₂, 4-Br-pyrazolyl-1 | Cl | —(CH₂)₂—CH(CH₃)—(CH₂)₂— | F | F | H | H | F | 131-134 |
| I-100 | 4-Cl-pyrazolyl-1 | Cl | —(CH₂)₂—CH(CH₃)—(CH₂)₂— | F | F | H | H | F | 150-152 | c-C₅H₉ = cyclopentyl
# denotes the bond with the pyrimidinyl skeleton of formula I The lipophilicity parameters $logP_{ow}$ (Table I) were determined as specified by OECD directive test guidelines using the RP-HPLC run time method.

To this end, a logk'/$logP_{ow}$ correlation curve based on ten reference substances was plotted and validated with the aid of the lipophilicity parameters of eight comparative substances, which had been established by the extraction method.

A commercially available reversed-phase C₁₈ stationary phase was used as stationary phase. Chromatographic separation was carried out with methanol and a buffer solution as mobile phase at pH 7.4 under isocratic conditions.

The retention times of the standards $t_R$ were converted in accordance with equation Φ into the capacity factors k', where $t_0$, as reaction time of the solvent unretarded on the reversed-phase C₁₈ stationary phase, represents the dead time of the chromatographic system:

$$k' = \frac{t_R - t_0}{t_0} \quad \Phi$$

The linear correlation of the logk' values with the $logP_{ow}$ values of the standards published in the appendix to the Directive 92/69/EEC yields the correlation curve through linear regression.

The lipophilicity parameters $logP_{ow}$ of the analytes were interpolated from the correlation curve of the standards after calculation of the logarithmic capacity logk'.

The validation of the RP-HPLC analytical method described, and of the standards used, is carried out with the aid of eight comparison active compounds, the distribution behavior of which was determined with the aid of the extraction method.

Examples for the Action Against Harmful Fungi

The fungicidal action of the compounds of the general formula I was demonstrated by the following experiments:

The active compounds were prepared, separately or together, as a 10% emulsion in a mixture of 70% by weight of cyclohexanone, 20% by weight of Nekanil® LN (Lutensol® AP6, wetting agent with emulsifying and dispersing action, based on ethoxylated alkylphenols) and 10% by weight of Wettol® EM (nonionic emulsifier, based on ethoxylated castor oil) and were diluted with water to give the desired concentration.

Use Example 1

Activity Against *Alternaria solani* on Tomatoes

Leaves of pot plants cv. "Große Fleischtomate St. Pierre" were sprayed to runoff point with an aqueous suspension prepared from a stock solution consisting of 10% of active compound, 63% of cyclohexanone and 27% of emulsifier. On the following day, the leaves were infected with an aqueous suspension of *Alternaria solani* zoospores in 2% Biomalz solution at a concentration of $0.17 \times 10^6$ spores/ml. The plants were subsequently placed in a water-vapor-saturated chamber at temperatures between 20 and 22° C. After 5 days, early blight in the untreated, but infected, control plants had developed to such an extent that the disease level could be determined visually in %.

In this test, the plants treated with 63 ppm of the active substances I-1, I-4, I-12 to I-14, I-19 bis I-23, I-29, I-31, I-32, I-35 to I-37, I-40, I-41, I-46, I-47, I-51, I-52, I-54 and I-60 showed no disease or a disease level of up to 7%, while the untreated plants showed a disease level of 100%.

Use Example 2

Curative Activity Against *Puccinia recondita* on Wheat (Wheat Leaf Rust)

Leaves of wheat seedlings cv. "Kanzler" in pots were dusted with leaf rust (*Puccinia recondita*) spores. Thereafter, the pots were placed for 24 hours into a chamber with high atmospheric humidity (90-95%) and 20 to 22° C. During this time, the spores germinated, and the germination tubes penetrated the plant tissue. On the next day, the infected plants were sprayed to runoff point with an aqueous active substance preparation prepared from a stock solution consisting of 10% of active substance, 63% of cyclohexanone and 27% of emulsifier. After the spray coating had dried on, the test plants were grown in the greenhouse for 7 days at temperatures between 20 and 22° C. and a relative atmospheric humidity of 65 to 70%. The extent of rust development on the leaves was then determined.

In this test, the plants treated with 63 ppm of the active substances I-1 and I-2 showed a disease level of not more than 7%, while the untreated plants showed a disease level of 90%.

Use Example 3

Activity Against Barley Net Blotch Disease

Leaves of barley seedlings cv. "Igri" in pots were sprayed to runoff point with an aqueous suspension prepared from a stock solution consisting of 10% of active substance, 63% of cyclohexanone and 27% of emulsifier and, 24 hours after the spray coating had dried on, inoculated with an aqueous spore suspension of *Pyrenophora teres*, the net blotch disease pathogen.

The test plants were subsequently placed in the greenhouse at temperatures between 20 and 24° C. and a relative atmospheric humidity of 95 to 100%. After 6 days, the extent of the disease level was determined visually in % diseased overall leaf area.

In this test, the plants which had been treated with 63 ppm of the active substances I-1, I-4, I-12 to I-14, I-19 to I-23, I-29, I-32, I-35 to I-37, I-40, I-41, I-47, I-51, I-52, I-54 and I-60 showed no disease or a disease level of up to 10%, while the untreated plants showed a disease level of 90%.

Use Example 4

Activity Against *Botrytis cinerea* on *Capsicum* Leaves

*Capsicum* seedlings cv. "Neusiedler Ideal Elite" were allowed to fully develop 4 to 5 leaves and then sprayed to runoff point with an aqueous active substance preparation which had been prepared from a stock solution consisting of 10% of active compound, 85% of cyclohexanone and 5% of emulsifier. On the next day, the treated plants were inoculated with a spore suspension of *Botrytis cinerea*, which contained $1.7 \times 10^6$ spores/ml in a 2% aqueous Biomalz solution. The test plants were subsequently placed into a control/environment cabinet at 22-24° C. and high atmospheric humidity. After 5 days, the extent of fungal infection on the leaves was determined visually in %.

In this test, the plants treated with 250 ppm of the active substances I-1, I-3, I-4, I-7 to I-9, I-11 to I-14, I-18 to I-23, I-29 to I-32, I-35 to I-37, I-40, I-47, I-51, I-52, I-54, I-60, I-77, I-78 and I-80 showed no disease or a disease level of up to 7%, while the untreated plants showed a disease level of 90%.

Use Example 5

Protective Activity Against Powdery Mildew of Cucumbers Caused by *Sphaerotheca fuliginea*

Leaves of cucumber seedlings cv. "Chinesiche Schlange" in pots were sprayed, at the cotyledon stage with an aqueous active substance preparation which had been made with a stock solution consisting of 10% active substance, 85% of cyclohexanone and 5% of emulsifier. 20 hours after the spray coating had dried on, the plants were inoculated with an aqueous spore suspension of cucumber powdery mildew (*Sphaerotheca fuliginea*). The plants were subsequently grown in the greenhouse for 7 days at temperatures between 20 and 24° C. and a relative atmospheric humidity of 60 to 80%. The extent of mildew development was then determined visually in % diseased cotyledon area.

In this test, the plants which had been treated with 63 ppm of the active substances I-1, I-4, I-12 to I-14, I-19 to I-23, I-29, I-31, I-32, I-35, I-36, I-41, I-47, I-52, I-54 and I-60 showed no disease, while the untreated plants showed a disease level of 100%.

We claim:
1. An intermediate of formula VI, VIa, VIII or IX

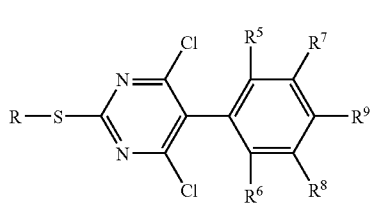

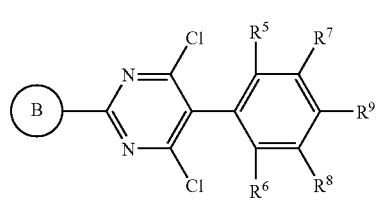

-continued

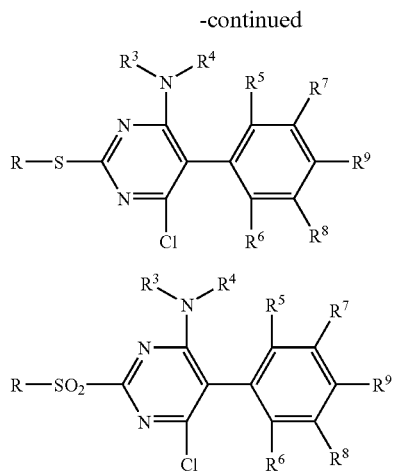

wherein

R is $C_1$-$C_6$-alkyl;

$R^3$, $R^4$ are, independently of one another, hydrogen, $C_1$-$C_6$-alkyl, $C_1$-$C_6$-haloalkyl, $C_3$-$C_6$-cycloalkyl, $C_3$-$C_6$-halocycloalkyl, $C_2$-$C_6$-alkenyl, $C_2$-$C_6$-haloalkenyl, $C_2$-$C_6$-alkynyl, or $C_2$-$C_6$-haloalkynyl, or $R^3$ and $R^4$ are, together with the nitrogen atom to which they are bonded, a five- or six-membered ring which can be interrupted by O and which can have attached to it a $C_1$-$C_6$-alkyl substituent;

(B)

is a five to ten-membered saturated, partially unsaturated or aromatic heterocycle consisting of carbon atoms and from one to four heteroatoms selected from the group consisting of O, N and S, which is bonded via carbon, and which is optionally substituted by one to three identical or different groups $R^a$;

$R^a$ is halogen, hydroxyl, cyano, oxo, nitro, amino, mercapto, $C_1$-$C_6$-alkyl, $C_1$-$C_6$-haloalkyl, $C_1$-$C_6$-alkenyl, $C_2$-$C_6$-alkynyl, $C_3$-$C_6$-cycloalkyl, $C_1$-$C_6$-alkoxy, $C_1$-$C_6$-haloalkoxy, carboxyl, $C_1$-$C_7$-alkoxycarbonyl, carbamoyl, $C_1$-$C_7$-alkylaminocarbonyl, $C_1$-$C_6$-alkyl-$C_1$-$C_6$-alkylaminocarbonyl, morpholinocarbonyl, pyrrolidinocarbonyl, $C_1$-$C_7$-alkylcarbonylamino, $C_1$-$C_6$-alkylamino, di($C_1$-$C_6$-alkyl)amino, $C_1$-$C_6$-alkylthio, $C_1$-$C_6$-alkylsulfinyl, $C_1$-$C_6$-alkylsulfonyl, hydroxysulfonyl, aminosulfonyl, $C_1$-$C_6$-alkylaminosulfonyl or di($C_1$-$C_6$-alkyl)aminosulfonyl; and the combination of the substituents $R^5$ to $R^9$ has the following meanings:

in formula VI: 2-chloro,6-fluoro; 2,6-difluoro; 2,6-dichloro; 2,4,6-trifluoro; 2,6-difluoro,4-methoxy and pentafluoro, in formula VIa: 2-chloro,6-fluoro; 2,6-difluoro; 2,6-dichloro; 2-methyl,6-fluoro; 2,4,6-trifluoro; 2,6-difluoro,4-methoxy; and pentafluoro, and in formulae VIII and IX: 2-chloro,6-fluoro; 2,6-difluoro; 2,6-dichloro; 2-methyl,6-fluoro; 2,4,6-trifluoro; 2,6-difluoro, 4-methoxy; and pentafluoro.

2. An intermediate defined in claim 1, wherein (B)

is pyrrole, pyrazole, imidazole, 1,2,4-triazole, 1,2,3-triazole, 1,2,3-triazine, 1,2,4-triazine, oxazole, isoxazole, 1,3,4-oxadiazole, thiazole, isothiazole, pyridazine, pyrimidine or pyrazine, which is bonded to the pyrimidine ring via carbon, and which is optionally substituted by one to three identical or different groups $R^1$, $R^a$ is halogen, hydroxyl, cyano, nitro, amino, mercapto, $C_1$-$C_6$-alkyl, $C_1$-$C_6$-haloalkyl, $C_2$-$C_6$-alkenyl, $C_2$-$C_6$-alkynyl, $C_3$-$C_6$-cycloalkyl, $C_1$-$C_6$-alkoxy, $C_1$-$C_6$-haloalkoxy, carboxyl, $C_1$-$C_7$-alkoxycarbonyl, carbamoyl, $C_1$-$C_7$-alkylaminocarbonyl, $C_1$-$C_6$-alkyl-$C_1$-$C_6$-alkylaminocarbonyl, morpholinocarbonyl, pyrrolidinocarbonyl, $C_1$-$C_7$-alkylcarbonylamino, $C_1$-$C_6$-alkylamino, di($C_1$-$C_6$-alkyl)amino, $C_1$-$C_6$-alkylthio, $C_1$-$C_6$-alkylsulfinyl, $C_1$-$C_6$-alkylsulfonyl, hydroxysulfonyl, aminosulfonyl, $C_1$-$C_6$-alkylaminosulfonyl or di($C_1$-$C_6$-alkyl)aminosulfonyl.

3. An intermediate defined in claim 1, wherein (B)

is pyrrole, pyrazole, imidazole, 1,2,4-triazole, 1,2,3-triazole, 1,2,3-triazine, 1,2,4-triazine, oxazole, isoxazole, 1,3,4-oxadiazole, thiazole, or isothiazole, which is bonded to the pyrimidine ring via carbon, and which is optionally substituted by one to three identical or different groups $R^a$, $R^a$ is halogen, hydroxyl, cyano, nitro, amino, mercapto, $C_1$-$C_6$-alkyl, $C_1$-$C_6$-haloalkyl, $C_2$-$C_6$-alkenyl, $C_2$-$C_6$-alkynyl, $C_3$-$C_6$-cycloalkyl, $C_1$-$C_6$-alkoxy, $C_1$-$C_6$-haloalkoxy, carboxyl, $C_1$-$C_7$-alkoxycarbonyl, carbamoyl, $C_1$-$C_7$-alkylaminocarbonyl, $C_1$-$C_6$-alkyl-$C_1$-$C_6$-alkylaminocarbonyl, morpholinocarbonyl, pyrrolidinocarbonyl, $C_1$-$C_7$-alkylcarbonylamino, $C_1$-$C_6$-alkylamino, di($C_1$-$C_6$-alkyl)amino, $C_1$-$C_6$-alkylthio, $C_1$-$C_6$-alkylsulfinyl, $C_1$-$C_6$-alkylsulfonyl, hydroxysulfonyl, aminosulfonyl, $C_1$-$C_6$-alkylaminosulfonyl or di($C_1$-$C_6$-alkyl)aminosulfonyl.

4. An intermediate defined in claim 1, wherein (B)

is pyrazole, pyrrole, imidazole, 1,2,3-triazole, or 1,2,4-triazole which is bonded to the pyrimidine ring via carbon, and which is optionally substituted by one to three identical or different groups $R^a$, $R^a$ is halogen, hydroxyl, cyano, nitro, amino, mercapto, $C_1$-$C_6$-alkyl, $C_1$-$C_6$-haloalkyl, $C_2$-$C_6$-alkenyl, $C_2$-$C_6$-alkynyl, $C_3$-$C_6$-cycloalkyl, $C_1$-$C_6$-alkoxy, $C_1$-$C_6$-haloalkoxy, carboxyl, $C_1$-$C_7$-alkoxycarbonyl, carbamoyl, $C_1$-$C_7$-alkylaminocarbonyl, $C_1$-$C_6$-alkyl-$C_1$-$C_6$-alkylaminocarbonyl, morpholinocarbonyl, pyrrolidinocarbonyl, $C_1$-$C_7$-alkylcarbonylamino, $C_1$-$C_6$-alkylamino, di($C_1$-$C_6$-alkyl)amino, $C_1$-$C_6$-alkylthio, $C_1$-$C_6$-alkylsulfinyl, $C_1$-$C_6$-alkylsulfonyl, hydroxysulfonyl, aminosulfonyl, $C_1$-$C_6$-alkylaminosulfonyl or di($C_1$-$C_6$-alkyl)aminosulfonyl.

5. An intermediate defined in claim 1, wherein
$R^3$, $R^4$ are, independently of one another, hydrogen, $C_1$-$C_6$-alkyl, $C_1$-$C_6$-haloalkyl, $C_3$-$C_6$-cycloalkyl or $C_2$-$C_6$-alkenyl, or
$R^3$ and $R^4$ are, together with the nitrogen atom to which they are bonded, a five or six-membered ring which can be interrupted by an oxygen atom and which can have attached to it a $C_1$-$C_6$-alkyl substituent.

6. An intermediate of formula VIa defined in claim 1, wherein the combination of the substituents $R^5$ to $R^9$ has the following meanings: 2-chloro,6-fluoro; 2,6-difluoro; 2,6-dichloro; 2-methyl,6-fluoro; 2,4,6-trifluoro; 2,6-difluoro,4-methoxy and pentafluoro.

7. An intermediate of formula VIII or IX defined in claim 1, wherein the combination of the substituents $R^5$ to $R^9$ has the following meanings: 2-chloro,6-fluoro; 2,6-difluoro; 2,6-dichloro; 2-methyl,6-fluoro; 2,4,6-trifluoro; 2,6-difluoro,4-methoxy; and pentafluoro.

8. An intermediate of formula VIa, VIII or IX defined in claim 1, wherein the combination of the substituents $R^5$ to $R^9$ has the following meanings: 2-chloro,6-fluoro; 2,6-difluoro; 2,6-dichloro; 2-methyl,6-fluoro; 2,4,6-trifluoro; 2,6-difluoro, 4-methoxy; and pentafluoro.

9. An intermediate of formula VIa

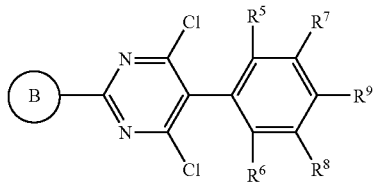

VIa wherein
R is $C_1$-$C_6$-alkyl;
$R^3$, $R^4$ are, independently of one another, hydrogen, $C_1$-$C_6$-alkyl, $C_1$-$C_6$-haloalkyl, $C_3$-$C_6$-cycloalkyl, $C_3$-$C_6$-halocycloalkyl, $C_2$-$C_6$-alkenyl, $C_2$-$C_6$-haloalkenyl, $C_3$-$C_6$-cycloalkenyl, $C_2$-$C_6$-alkynyl, $C_2$-$C_6$-haloalkynyl or $C_3$-$C_6$-cycloalkynyl, or
$R^3$ and $R^4$ are, together with the nitrogen atom to which they are bonded, a five or six-membered ring which can be interrupted by a hetero atom selected from the group consisting of O, N and S and/or which can have attached to it one or more substituents selected from the group consisting of halogen, $C_1$-$C_6$-alkyl, $C_1$-$C_6$-haloalkyl and oxy-$C_1$-$C_3$-alkylenoxy or in which two adjacent C atoms or one N atom and one adjacent C atom can be linked by a $C_1$-$C_4$-alkylene chain;

B is a five to ten-membered saturated, partially unsaturated or aromatic heterocycle consisting of carbon atoms and from one to four heteroatoms selected from the group consisting of O, N and S, which is bonded via carbon, and which is optionally substituted by one to three identical or different groups $R^a$;

$R^a$ is halogen, hydroxyl, cyano, oxo, nitro, amino, mercapto, $C_1$-$C_6$-alkyl, $C_1$-$C_6$-haloalkyl, $C_1$-$C_6$-alkenyl, $C_2$-$C_6$-alkynyl, $C_3$-$C_6$-cycloalkyl, $C_1$-$C_6$-alkoxy, $C_1$-$C_6$-haloalkoxy, carboxyl, $C_1$-$C_7$-alkoxycarbonyl, carbamoyl, $C_1$-$C_7$-alkylaminocarbonyl, $C_1$-$C_6$-alkyl-$C_1$-$C_6$-alkylaminocarbonyl, morpholinocarbonyl, pyrrolidinocarbonyl, $C_1$-$C_7$-alkylcarbonylamino, $C_1$-$C_6$-alkylamino, di($C_1$-$C_6$-alkyl)amino, $C_1$-$C_6$-alkylthio, $C_1$-$C_6$-alkylsulfinyl, $C_1$-$C_6$-alkylsulfonyl, hydroxysulfonyl, aminosulfonyl, $C_1$-$C_6$-alkylaminosulfonyl or di($C_1$-$C_6$-alkyl)aminosulfonyl; and the combination of the substituents $R^5$ to $R^9$ has the following meanings:
2-chloro,6-fluoro; 2,6-difluoro; 2,6-dichloro; 2-methyl,4-fluoro; 2-methyl,6-fluoro; 2-fluoro,4-methyl; 2,4,6-trifluoro; 2,6-difluoro,4-methoxy; 2,4-dimethyl and pentafluoro.

* * * * *

UNITED STATES PATENT AND TRADEMARK OFFICE
CERTIFICATE OF CORRECTION

PATENT NO. : 7,709,637 B2  Page 1 of 1
APPLICATION NO. : 11/548864
DATED : May 4, 2010
INVENTOR(S) : Grote et al.

It is certified that error appears in the above-identified patent and that said Letters Patent is hereby corrected as shown below:

In Claim 2, col. 38, indicated line 13:
"different groups $R^1$" should read -- different groups $R^a$ --

Signed and Sealed this

First Day of June, 2010

David J. Kappos
*Director of the United States Patent and Trademark Office*